US012758686B1

(12) United States Patent
Reynard

(10) Patent No.: US 12,758,686 B1
(45) **Date of Patent: *Oct. 13, 2026**

(54) ENDOTHELIAL-INTEGRATED STENT FOR SCHLEMM'S CANAL

(71) Applicant: Michael Reynard, Santa Monica, CA (US)

(72) Inventor: Michael Reynard, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/343,026

(22) Filed: Sep. 29, 2025

Related U.S. Application Data

(63) Continuation-in-part of application No. 19/190,443, filed on Apr. 25, 2025, now Pat. No. 12,458,535.

(51) Int. Cl.

| | |
|---|---|
| ***A61L 31/04*** | (2006.01) |
| ***A61F 9/007*** | (2006.01) |
| ***A61L 31/00*** | (2006.01) |
| ***A61L 31/08*** | (2006.01) |
| ***A61L 31/10*** | (2006.01) |
| ***A61L 31/14*** | (2006.01) |
| ***A61L 31/16*** | (2006.01) |
| ***A61L 31/18*** | (2006.01) |

(Continued)

(52) U.S. Cl.
CPC ........ *A61L 31/041* (2013.01); *A61F 9/00781* (2013.01); *A61L 31/005* (2013.01); *A61L 31/088* (2013.01); *A61L 31/10* (2013.01); *A61L 31/146* (2013.01); *A61L 31/148* (2013.01); *A61L 31/16* (2013.01); *A61L 31/18* (2013.01); *C08L 67/04* (2013.01); *C08L 71/02* (2013.01); *A61L 2300/41* (2013.01); *A61L 2300/64* (2013.01)

(58) Field of Classification Search
CPC .................... A61F 9/00781; A61F 2/91; A61F 2250/0067; A61L 31/005; A61L 31/146; A61L 31/16
See application file for complete search history.

(56) References Cited

U.S. PATENT DOCUMENTS

| | | | |
|---|---|---|---|
| 6,626,858 | B2 | 9/2003 | Lynch et al. |
| 6,893,458 | B2 | 5/2005 | Cox et al. |
| 7,740,604 | B2 | 6/2010 | Schieber et al. |

(Continued)

FOREIGN PATENT DOCUMENTS

| | | | |
|---|---|---|---|
| AU | 2020204391 | B2 | 12/2021 |
| CA | 2759015 | C | 10/2010 |

(Continued)

OTHER PUBLICATIONS

U.S. Appl. No. 77/018,711, filed May 4, 2010, Hosheng Tu, et al.

(Continued)

*Primary Examiner* — Leslie R Deak
(74) *Attorney, Agent, or Firm* — Richard A Baker, Jr.

(57) ABSTRACT

A bioengineered endothelial stent designed for implantation in Schlemm's canal enhances aqueous humor outflow and restores physiological intraocular pressure regulation. Unlike conventional devices, this stent integrates transplanted Schlemm's canal endothelial cells (SCECs) to restore mechanosensitive outflow regulation. The stent features a biocompatible or biodegradable scaffold with an endothelial cell-seeding system to support integration into the Schlemm's canal inner wall. This regenerative approach maintains physiological resistance and prevents excessive drainage, offering a stable, cell-based alternative to conventional glaucoma stents.

30 Claims, 17 Drawing Sheets

(51) Int. Cl.
*C08L 67/04* (2006.01)
*C08L 71/02* (2006.01)

(56) References Cited

U.S. PATENT DOCUMENTS

| | | | |
|---|---|---|---|
| 7,803,183 | B2 | 9/2010 | Kutryk et al. |
| 7,803,558 | B2 | 9/2010 | Stamer et al. |
| 7,887,871 | B2 | 2/2011 | Dehnad |
| 8,337,509 | B2 | 12/2012 | Schieber et al. |
| 8,372,026 | B2 | 2/2013 | Schieber et al. |
| 8,425,449 | B2 | 4/2013 | Wardle et al. |
| 8,512,404 | B2 | 8/2013 | Frion et al. |
| 8,579,846 | B2 | 11/2013 | Tu et al. |
| 8,663,150 | B2 | 3/2014 | Wardle et al. |
| 8,734,377 | B2 | 5/2014 | Schieber et al. |
| 8,876,898 | B2 | 11/2014 | Badawi et al. |
| 8,894,578 | B2 | 11/2014 | Wong et al. |
| 8,961,447 | B2 | 2/2015 | Schieber et al. |
| 9,005,897 | B2 | 4/2015 | Lim et al. |
| 9,039,650 | B2 | 5/2015 | Schieber et al. |
| 9,050,169 | B2 | 6/2015 | Schieber et al. |
| 9,066,782 | B2 | 6/2015 | Tu et al. |
| 9,211,213 | B2 | 12/2015 | Wardle et al. |
| 9,226,852 | B2 | 1/2016 | Schieber et al. |
| 9,351,874 | B2 | 5/2016 | Schieber et al. |
| 9,402,767 | B2 | 8/2016 | Schieber et al. |
| 9,486,361 | B2 | 11/2016 | Badawi et al. |
| 9,610,196 | B2 | 4/2017 | Schieber et al. |
| 9,693,899 | B2 | 7/2017 | Wardle et al. |
| 9,752,119 | B2 | 9/2017 | Gamm et al. |
| 9,789,001 | B2 | 10/2017 | Tu et al. |
| 10,004,766 | B2 | 6/2018 | Du et al. |
| 10,154,924 | B2 | 12/2018 | Clauson et al. |
| 10,780,130 | B2 | 9/2020 | Phan et al. |
| 10,993,840 | B2 | 5/2021 | Berlin |
| 11,363,951 | B2 | 6/2022 | Burns et al. |
| 11,707,383 | B2 | 7/2023 | Liang et al. |
| 11,838,958 | B2 | 12/2023 | Wang et al. |
| 11,903,875 | B2 | 2/2024 | Kancerevycius et al. |
| 11,944,573 | B2 | 4/2024 | Haffner et al. |
| 12,054,719 | B2 | 8/2024 | Humphries et al. |
| 12,221,621 | B2 | 2/2025 | Dvir et al. |
| 12,232,987 | B2 | 2/2025 | Armstrong et al. |
| 12,232,989 | B2 | 2/2025 | Andersson et al. |
| 12,239,412 | B2 | 3/2025 | Petroff et al. |
| 2004/0167076 | A1 | 8/2004 | Stamer et al. |
| 2009/0036818 | A1 | 2/2009 | Grahn et al. |
| 2015/0051699 | A1 | 2/2015 | Badawi et al. |
| 2018/0028361 | A1 | 2/2018 | David et al. |
| 2019/0017017 | A1 | 1/2019 | Xie et al. |
| 2024/0108635 | A1 | 4/2024 | Ghebremeskel et al. |
| 2024/0189147 | A1 | 6/2024 | Romoda |
| 2024/0293260 | A1 | 9/2024 | Schieber et al. |
| 2025/0072837 | A1 | 3/2025 | Black et al. |

FOREIGN PATENT DOCUMENTS

| | | | |
|---|---|---|---|
| EP | 2517619 | B1 | 5/2013 |
| WO | 2022062050 | A1 | 3/2022 |

OTHER PUBLICATIONS

Gonzalez, J. M., Ko, M. K., Hong, Y. K., & Tan, J. C. (2016). Generation of Schlemm's canal-like endothelial cells from human stem cells. Stem Cells Translational Medicine, 5(11), 1530-1545. https://doi.org/10.5966/sctm.2016-0047.

Zhang, Y., Yang, G., et al. (2018). Deep learning for glaucoma detection and screening using OCT images. IEEE Journal of Biomedical and Health Informatics, 22(5), 1566-1577. https://doi.org/10.1109/JBHI.2018.2791898.

Johnson, Mark and Stamer, W.D. (2015). Therapeutically Targeting Disease in Glaucoma. Glaucoma Today. May/Jun. 2015, 12-14.

Dautriche, Cula N., Tian, Y., Xie, Y., and Sharfstein, T. J. Funct. Biomater. (2015), 6, 963-985; doi: 10.3390/jfb6030963.

Huang, A.S., Camp, A., Xu, B.Y., Penteado, R.C., and Weinreb, R.N. (2017). Aqueous angiography: Aqueous humor outflow imaging in live human subjects. Ophthalmology, 124(8), 1249-1251.doi: 10.1016/j.ophtha.2017.02.025.

Kelly, R.A., Perkumas, K.M., Campbell, M., Farrar, G.J., Stamer, W.D., Humphries, P., O'Callaghhan, J., & O'Brien, C. J. Fibrotic changes to Schlemm's canal endothelial cells in glaucoma. Int. J. Mol. Sci. (2021). Aug. 31;22(17):9446. doi: 10.3390/ijms22179446.

Konopińska, K., Lewczuk, K., Jabłońska, J., Mariak, Z., Rkas, M. (2021) Microinvasive Glaucoma Surgery: A Review of Schlemm's Canal-Based Procedures, Clinical Ophthalmology, 15, 1109-1118. DOI: 10.2147/OPTH.S253984.

Overby, D. R., Stamer, W. D., & Johnson, M. (2014). Regeneration of Schlemm's canal endothelium as a strategy for glaucoma treatment. Investigative Ophthalmology & Visual Science, 55(3), 188-198. https://doi.org/10.1167/iovs. 14-14677.

Saraswathy, S., Tan, J. C., Yu, F., Francis, B.F., Hinton, D.R., Weinreb, R.N., Huang, A.S. (2016). Aqueous angiography: Real-time and physiologic aqueous humor outflow imaging. PLOS ONE, 11(1), e0147176. doi: 10.1371/journal.pone.0147176.

Stamer, W.D., Braakman, S.T., Zhou, E., Ethier, CR., Fredberg, J.J., Overby, D.R., Johnson, M. (2015) Biomechanics of Schlemm's canal endothelium and intraocular pressure reduction. Prog. Retin Eye Res., 0:86-98. doi: 10.1016/j.preteyeres. 2014.08.002.

ENDOTHELIAL-INTEGRATED STENT FOR SCHLEMM'S CANAL

CROSS-REFERENCE TO RELATED APPLICATIONS

This document is a continuation-in-part of U.S. patent application Ser. No. 19/190,443, filed by the inventor on Apr. 25, 2025, said application incorporated herein in its entirety.

BACKGROUND

Field of the Inventions

The present inventions relate to ophthalmic devices, particularly to an implantable stent for Schlemm's canal designed for endothelial cell delivery and integration. The stent restores aqueous humor outflow by improving Schlemm's canal endothelial function, reducing intraocular pressure (IOP) in patients with primary open-angle glaucoma (POAG) and other outflow disorders.

Background

Schlemm's canal is a circumferential endothelial-lined vessel located at the interface of the trabecular Meshwork™ and aqueous humour outflow pathways. Schlemm's canal plays a fundamental role in regulating intraocular pressure by facilitating aqueous humor outflow.

Schlemm's canal endothelium has distinct characteristics. Endothelial cells lining the inner wall facilitate transport from the trabecular meshwork into the canal lumen via paracellular functions, transcellular pores, and giant vacuole-mediated flow. Junctional complexes between endothelial cells in Schlemm's canal form specialized tight junctions with discontinuous characteristics, allowing for controlled permeability and regulation of aqueous humor outflow. Aqueous humor transport is therefore facilitated by a combination of biologic factors that include junctional regulation, transcellular pores, and giant vacuoles.

Intraocular pressure from the anterior chamber percolates through the trabecular meshwork to exert pressure against the inner wall of endothelial cells lining Schlemm's canal. This causes the endothelial cells to bend inward and form aqueous-filled pockets known as giant vacuoles. Depending on pressure changes, these vacuoles undergo expansion and contraction. The giant vacuoles temporarily store aqueous humor before the fluid is released through the walls of the endothelium through pores and into Schlemm's canal. Thus, the storage of aqueous fluid serves as a temporary reservoir that adjusts to changes of intraocular pressure and regulates aqueous humor outflow.

Endothelial pore size, density, and function play an important role in regulating intraocular pressure. The quantity of pores is directly related to intraocular pressure. A lower intraocular pressure is enabled with a high number of pores and decreased pore density is associated with increased resistance to aqueous flow and elevated intraocular pressure. Disease and loss of endothelial pores lining Schlemm's canal is caused by aging, fibrosis, inflammation, oxidative stress, and chronically elevated levels of intraocular pressure. Loss of function and density of endothelial pores in Schlemm's canal can result in increased outflow resistance with elevated intraocular pressure.

Schlemm's canal stents for the treatment of glaucoma are often successful at reducing intraocular pressure and are believed to pose minimal risk of widespread loss of endothelial cells. However, these stents can reduce giant vacuole formation when they alter shear stress or compress endothelial cells against the outer wall. Efforts to restore giant vacuoles and endothelial pores in Schlemm's canal have primarily involved experimental approaches, including Rho-kinase inhibitors to enhance endothelial cell permeability and promote giant vacuole formation, prostaglandin analogs to stimulate giant vacuole activity, and nitric oxide to improve pore permeability and endothelial function.

Endothelial cells exhibit inherent migratory capacity in response to biochemical signals and mechanical stimuli. When placed in an environment that mimics natural extracellular matrix (ECM) cues, these cells may extend their migration into collector channels, contributing to the formation of a continuous endothelial lining.

The extent of endothelial migration is strongly influenced by substrate properties. A stent featuring a bioactive surface—engineered to promote cell adhesion and localized gradients of adhesion molecules or growth factors—can facilitate the outward expansion of transplanted endothelial cells beyond the initial implantation site. Additionally, local fluid dynamics, including the shear stress exerted by aqueous humor flow and pressure gradients within Schlemm's canal, serve as key regulatory factors in guiding endothelial migration into structural defects or areas of endothelial loss within Schlemm's canal and its associated collector channels.

The first proof of concept for Schlemm's canal endothelial regeneration as a strategy for treating glaucoma was published by Overby et al. in 2014. These authors provided evidence that the cultured endothelial cells from Schlemm's canal were able to integrate into Schlemm's canal in vitro. In 2016, Gonzales et al. showed stem cells derived from Schlemm's can were able to differentiate into cells that formed giant vacuoles and pores. Their study formed a foundation for therapies using cell-based strategies.

Glaucoma treatment has long relied on surgical devices such as trabeculectomy, drainage implants, and Schlemm's canal stents, yet these approaches often produce unpredictable intraocular pressure reduction due to variations in wound healing, fibrosis, and aqueous humor dynamics. To address this limitation, we propose a novel bioengineered stent designed not only to enhance outflow but also to restore the natural function of Schlemm's canal through endothelial cell transplantation.

Unlike conventional stents, which passively bypass trabecular meshwork outflow resistance, this device actively integrates transplanted Schlemm's canal endothelial cells (SCECs) onto the inner wall of Schlemm's canal, promoting giant vacuole formation, transcellular pore development, and physiologic outflow regulation. By leveraging cell-based regeneration, this approach seeks to revitalize the compromised endothelial barrier, offering a more sustained and predictable intraocular pressure-lowering effect while preserving the eye's natural drainage architecture. This represents a shift in glaucoma therapy, moving beyond mechanical drainage solutions toward biological restoration of the tissue responsible for long-term intraocular pressure control.

Aqueous within Schlemm's canal drains through various pathways, including a myriad of about 75 collector channels that extend from the outer wall of the canal. Aqueous from the collector channels drains into the episcleral venous system. The average length of a collector channel is between 0.05 to 0.3 mm. The average ostial opening of a collector channel is 0.1 to 0.2 microns. The stent may be implanted at any location within Schlemm's canal, though the superotemporal and inferonasal regions are preferred due to their density of collector channels.

The development of glaucoma is caused by a number of factors associated with elevated intraocular pressure. Fibrosis of the trabecular meshwork can restrict aqueous from passing through the trabecular meshwork and entering Schlemm's canal. Dysfunction or loss of endothelial cells in Schlemm's canal contributes to increased outflow resistance and is implicated in primary open-angle glaucoma (POAG). Endothelial dysfunction in Schlemm's canal can also lead to reduced pore formation, fibrosis, and outflow resistance, contributing to the elevation of intraocular pressure. Prolonged elevated pressure is linked to injury of the optic nerve and loss of visual field. The diagnosis of glaucoma is based on this triad of signs.

Conventional surgical treatment includes a wide number of devices that create new drainage pathways for aqueous humor. However, these devices are often plagued by failure to adequately control intraocular pressure, scar tissue that blocks openings created by devices, hypotony, hyphema, or infection. Endothelial cell transplantation to Schlemm's canal is a method that provides a natural approach to restoration of improved flow of aqueous humor to control intraocular pressure and help prevent vision loss from glaucoma.

BRIEF SUMMARY

In one aspect, an apparatus includes a bioengineered stent configured for insertion in Schlemm's canal, a biocompatible or biodegradable scaffold affixed to the bioengineered stent, endothelial cells adhered to the biocompatible or biodegradable scaffold, and a cell-seeding system promoting endothelial cell adhesion and functional integration on the exterior surface of the bioengineered stent.

The apparatus may also include micropores on the bioengineered stent. The apparatus may also include a microporous structure where the micropores range from 0.5-2 microns to replicate endothelial permeability, and the micropores that are uniformly distributed or asymmetrically positioned to direct aqueous outflow. The biocompatible or biodegradable scaffold may include a titanium oxide coating, a nitric oxide-releasing polymer, and an ECM protein layer (fibronectin, laminin, collagen IV). The biocompatible or biodegradable scaffold may include poly(lactic-co-glycolic acid) (PLGA). The biocompatible or biodegradable scaffold may include a hybrid structure having a core of nitinol. The biocompatible or biodegradable scaffold may include a hybrid structure having a self-expanding nitinol core configured to provide mechanical support and conformability within Schlemm's canal. The biocompatible or biodegradable scaffold may include an outer bioabsorbable layer selected from a group consisting of poly(lactic-co-glycolic acid) (PLGA) and polyethylene glycol (PEG), where the outer bioabsorbable layer degrades over a period of 3 to 12 months. The hybrid embodiment stent 702 is comprised of a nitinol core with distal-only PLGA cladding configured to degrade over time while maintaining structural integrity. The biocompatible or biodegradable scaffold may be composed of cross-linked polyethylene glycol (PEG) hydrogel, having a degradation time of 2 weeks to 3 months. The biocompatible or biodegradable scaffold may include polydimethylsiloxane (PDMS) microstructures, providing a degradation profile of 6 to 18 months. The biocompatible or biodegradable scaffold may include a bioabsorbable polymer selected from a group consisting of poly(lactic-co-glycolic acid) (PLGA), polyethylene glycol (PEG) hydrogel, or polydimethylsiloxane (PDMS), and where the biocompatible or biodegradable scaffold degrades over time. The apparatus may also include an embedded drug delivery system within the biocompatible or biodegradable scaffold, where a nitric oxide-releasing compound is released over 1-3 months, and a vascular endothelial growth factor (VEGF) component is released over 3-6 months.

The cell-seeding system may include either in vitro bioreactor preconditioning before implantation, or in vivo migration and proliferation after placement.

The endothelial cells may be preconditioned prior to implantation with an in vitro bioreactor. The bioengineered stent may be seeded with the endothelial cells selected from a group consisting of mature Schlemm's canal endothelial cells, endothelial progenitor cells (EPCs), or stem cell-derived endothelial-like cells. The endothelial cells may be conditioned under physiological Schlemm's canal-like shear stress prior to implantation. The endothelial cells may be conditioned in a bioreactor under physiological Schlemm's canal-like shear stress conditions prior to implantation. The endothelial progenitor cells may be cultured with growth factors selected from a group consisting of vascular endothelial growth factor (VEGF), basic fibroblast growth factor (bFGF), and nitric oxide-releasing compound. The endothelial cells may be subjected to gradually increasing shear stress post-implantation. The endothelial cells may be seeded onto the bioengineered stent to stimulate native Schlemm's canal endothelial cell migration and repopulation.

The apparatus may also include that a delivery system includes an introducer cannula and a deployment mechanism for insertion of the bioengineered stent into Schlemm's canal. The apparatus may also include a delivery system that includes a microcatheter-assisted deployment mechanism for insertion of the bioengineered stent into Schlemm's canal, and a hydrogel-based injector that dissolves in aqueous humor. The apparatus may also include an extracellular matrix (ECM) coating selected from a group consisting of fibronectin, laminin, collagen IV, and heparan sulfate proteoglycans to promote endothelial adhesion and differentiation. The apparatus may also include that a degradation time is controlled by adjusting the ratio of lactic acid to glycolic acid in a group consisting of poly(lactic-co-glycolic acid) (PLGA) composition.

OCT imaging may be used to identify shear stress distribution along Schlemm's canal. In one aspect, a bioengineered endothelial-seeded stent for Schlemm's canal includes a biocompatible or biodegradable scaffold, a stent-seeding system promoting endothelial adhesion, functional integration, and micropores configured for pressure-responsive aqueous humor drainage. The bioengineered endothelial-seeded stent may also include a biocompatible or biodegradable scaffold that includes a nitinol frame with a self-expanding structure, and a biodegradable polymer (poly (lactic-co-glycolic acid) (PLGA), polyethylene glycol (PEG), polydimethylsiloxane (PDMS)) with a controlled degradation profile. The bioengineered endothelial-seeded stent may also include the biocompatible or biodegradable scaffold that includes both a permanent and a bioabsorbable layer. The bioengineered endothelial-seeded stent may also include the biocompatible or biodegradable scaffold that includes a titanium oxide coating, a nitric oxide-releasing polymer, and an ECM protein layer (fibronectin, laminin, collagen IV). The bioengineered endothelial-seeded stent may also include a microporous structure in the walls of the bioengineered endothelial-seeded stent where the micropores range from 0.5-2 μm to replicate endothelial permeability, and the micropores are uniformly distributed or asymmetrically positioned to direct aqueous outflow.

In one aspect, an endothelial-seeded stent for implantation in Schlemm's canal includes a biocompatible or bioabsorbable scaffold configured to support endothelial cell adhesion and function, a plurality of micropores configured to facilitate controlled aqueous humor outflow, where the endothelial-seeded stent is seeded with endothelial cells selected from a group consisting of Schlemm's canal endothelial cells (SCECs), Endothelial progenitor cells (EPCs) capable of differentiating into Schlemm's canal-like endothelial cells, or a combination thereof, where the endothelial cells are conditioned to enhance integration and function within Schlemm's canal.

In one aspect, a method for monitoring an integration and function of endothelial cells on an implanted stent in Schlemm's canal includes acquiring structural optical coherence tomography (OCT) images of the implanted stent and adjacent tissue, evaluating endothelial coverage of a surface of the implanted stent, and identifying morphologic endothelial configurations selected from a group consisting of multilayered endothelial formations, bridging patterns, pore formation, and vacuole development.

The method may also include using OCT imaging to assess changes in endothelial cell morphology over time, including thickness variation, curvature deformation, or formation of endothelial cell clusters indicative of shear-stress responsiveness. The method may also include where OCT is used to visualize an interface between an endothelial layer and collector channel ostia, without affecting the placement or navigation of the implanted stent.

In one aspect, a method for assessing fluid dynamics and endothelial-mediated flow regulation in Schlemm's canal includes: performing optical coherence tomography angiography (OCTA) to visualize motion-contrast patterns of aqueous humor flow, detecting regions of pulsatile flow, flow segmentality, or reduced perfusion within Schlemm's canal or collector channels, and correlating these patterns with endothelial remodeling or integration states.

The OCTA may reveal endothelial-related flow modulation, including flow dampening, transient stagnation, or segmental enhancement, attributable to endothelial vacuole activity or cellular redistribution. The OCTA may be used to compare flow patterns pre- and post-endothelial seeding, whereby alterations in segmental flow distribution are attributed to endothelial-mediated modulation.

In one aspect, a method of characterizing a physiologic behavior of transplanted or seeded endothelial cells on a stent implanted in Schlemm's canal, includes: acquiring structural OCT and OCTA images at two or more timepoints post-implantation, detecting changes in stromal or endothelial reflectivity patterns overlying the stent, and using these imaging patterns to monitor dynamic endothelial behavior selected from a group consisting of pore reconstitution, vacuole expansion, and circumferential migration.

In one aspect, a method for detecting subclinical endothelial dysfunction in a stent-implanted Schlemm's canal using optical coherence tomography (OCT), includes: acquiring OCT images, identifying morphologic signatures suggestive of reduced endothelial integration or early fibrosis, including surface irregularity, thinning, or hyperreflective deposits near an interface between a stent and tissue, acquiring OCT angiography (OCTA) data, assessing motion-contrast signals near a periphery of the stent, where absence or attenuation of such signals further supports a presence of impaired aqueous flow or early endothelial compromise, and displaying a diagnosis of the presence of impaired aqueous flow or the early endothelial compromise.

In one aspect, an apparatus is described that includes a biocompatible or biodegradable stent for implantation in Schlemm's canal, where the stent is configured to support endothelial cell adhesion and function, and where the stent comprises a microporous structure to facilitate controlled aqueous humor outflow.

In one aspect, an apparatus includes a bioengineered stent configured for insertion in Schlemm's canal, a biocompatible polymer scaffold, coated with collagen, affixed to the bioengineered stent, endothelial cells adhered to the biocompatible polymer scaffold, and a cell-seeding system promoting endothelial cell adhesion and functional integration on an exterior surface of the bioengineered stent.

The biocompatible polymer scaffold may include fenestrated flow channels aligned with an anatomical curvature of Schlemm's canal. The biocompatible polymer scaffold may include surface ridges or microchannels.

The biocompatible polymer scaffold may include a titanium oxide coating. The biocompatible polymer scaffold may include poly(L-lactic acid) (PLLA). The biocompatible polymer scaffold may include cross-linked polyethylene glycol (PEG) hydrogel.

The bioengineered stent may be seeded with the endothelial cells selected from a group consisting of mature Schlemm's canal endothelial cells, endothelial progenitor cells (EPCs), or stem cell-derived endothelial-like cells. The biocompatible polymer scaffold may be configured for visualization using optical coherence tomography (OCT), such that the biocompatible polymer scaffold permits in vivo imaging of endothelial coverage post-implantation. The biocompatible polymer scaffold may be coated with laminin or fibronectin. The biocompatible polymer scaffold may include a surface coating of extracellular matrix proteins.

The biocompatible polymer scaffold may include a drug-eluting matrix releasing mitomycin C. The bioengineered stent may be configured for minimized trauma during delivery via microcatheter insertion. The endothelial cells may be derived from human Schlemm's canal tissue. A polymer in the biocompatible polymer scaffold may be a hybrid composite of silicone and polycaprolactone (PCL). The biocompatible polymer scaffold may be sterilized using gamma irradiation prior to cell seeding. The biocompatible polymer scaffold may include a therapeutic coating that includes anti-inflammatory agents. The biocompatible polymer scaffold may include a retention ring. The apparatus may also include micropores on the bioengineered stent.

In one aspect, a bioengineered endothelial-seeded stent for Schlemm's canal includes a biocompatible polymer scaffold coated with collagen, a stent-seeding system promoting endothelial adhesion and functional integration, and micropores configured for pressure-responsive aqueous humor drainage.

The biocompatible polymer scaffold may include a nitinol frame with a self-expanding structure, and a biodegradable polymer selected from the group consisting of poly(lactic-co-glycolic acid) (PLGA), polyethylene glycol (PEG), or polydimethylsiloxane (PDMS), each with a controlled degradation profile. The biocompatible polymer scaffold may include both a permanent and a bioabsorbable layer. The biocompatible polymer scaffold may include a titanium oxide coating. The bioengineered endothelial-seeded stent may also include a microporous structure in the walls of the bioengineered endothelial-seeded stent, where the micropores may range from 0.5-2 μm, and the micropores may be uniformly distributed. The bioengineered endothelial-seeded stent may also include a microporous structure in the walls of the bioengineered endothelial-seeded stent, where the micropores may range from 0.5-2 μm, and the micropores may be asymmetrically positioned.

In one aspect, an endothelial-seeded stent for implantation in Schlemm's canal, includes a biocompatible polymer scaffold coated with collagen configured to support endothelial cell adhesion and function, a plurality of micropores configured to facilitate controlled aqueous humor outflow, where the endothelial-seeded stent is seeded with endothelial cells selected from a group consisting of Schlemm's canal endothelial cells (SCECs), endothelial progenitor cells (EPCs) capable of differentiating into Schlemm's canal-like endothelial cells, or a combination thereof, where the endothelial cells are conditioned to enhance integration and function within Schlemm's canal.

The micropores may range from 0.5-2 microns, and the micropores may be uniformly distributed. The micropores may range from 0.5-2 microns, and the micropores may be asymmetrically positioned. The poly(L-lactic acid (PLLA) may be configured to degrade over a period of three to six months. The cross-linked polyethylene glycol (PEG) hydrogel may have a degradation time of two weeks to three months. The biocompatible polymer scaffold may be optimized for swept-source OCT.

Other technical features may be readily apparent to one skilled in the art from the following figures, descriptions, and claims.

BRIEF DESCRIPTION OF THE DRAWINGS

To easily identify the discussion of any particular element or act, the most significant digit or digits in a reference number refer to the figure number in which that element is first introduced.

DETAILED DESCRIPTION

Figure 1:
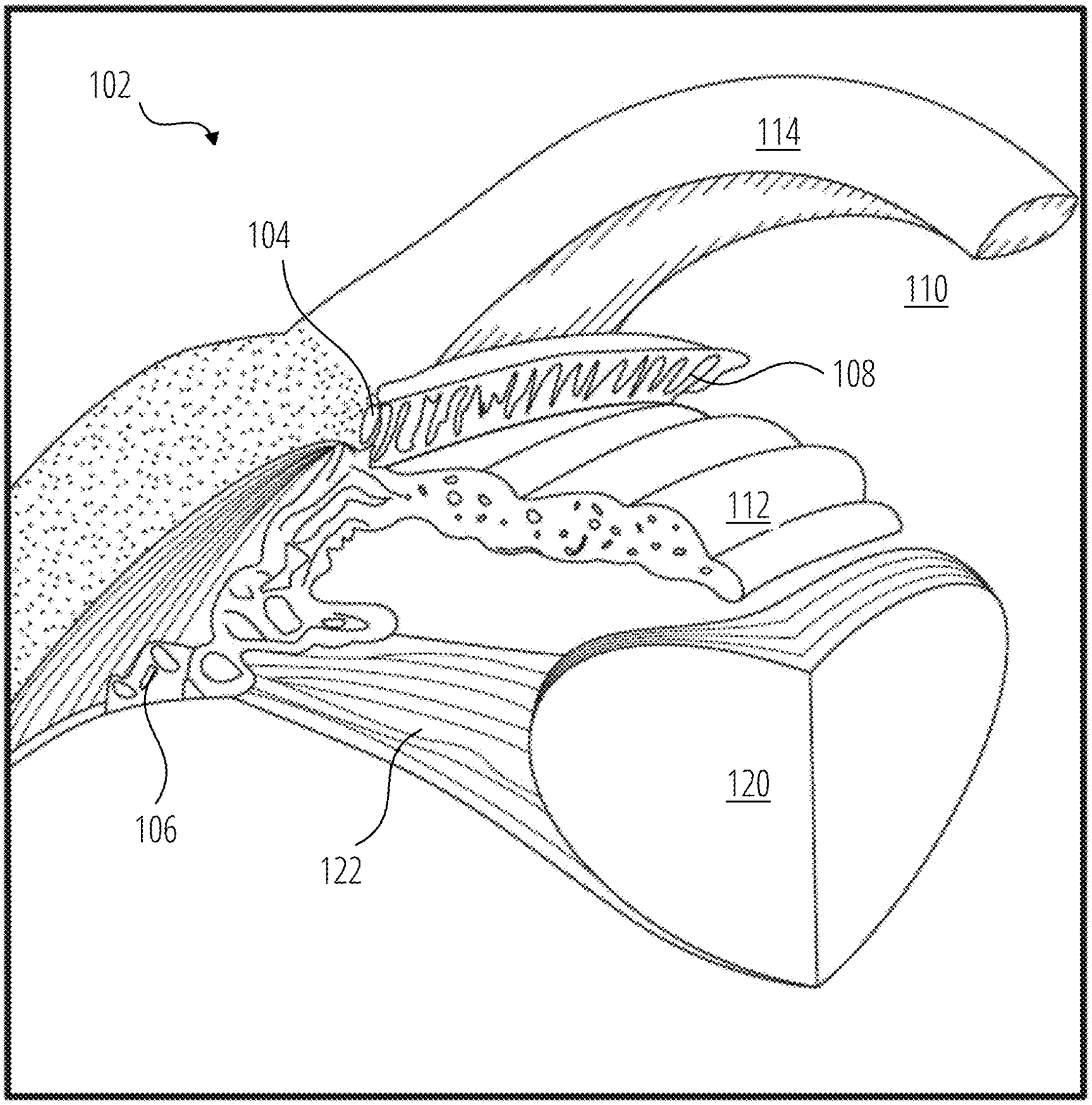
FIG. 1 illustrates the key anatomic landmarks in the eye.

A bioengineered endothelial stent 118, implanted in Schlemm's canal 104, enhances aqueous fluid 204 outflow and restores physiological intraocular pressure regulation in glaucoma patients. Unlike conventional devices with unpredictable intraocular pressure-lowering effects, this endothelial stent 118 incorporates transplanted Schlemm's canal endothelial cells 1402 (SCECs) to promote giant vacuole 1404 formation, mechanosensitive pore activity, and flow-regulated outflow control.

Throughout this document, the term endothelial stent 118 is used to refer to the many stents 502, 304, 402, 702, 802, 1002, 1102, 1202 individually and as a group. Each of these endothelial stents 118 could be coated with endothelial cells 1402 using any of the methods described below.

The device comprises a biocompatible or biodegradable scaffold engineered to conform to Schlemm's canal 104 and a cell-seeding system that promotes endothelial cell 1402 adhesion and functional integration onto the inner wall 1514 of Schlemm's canal 104. By restoring physiological resistance to aqueous fluid 204 outflow, the endothelial stent 118 prevents excessive drainage while ensuring sustained, predictable intraocular pressure reduction.

The inventions further include methods for endothelial cell 1402 isolation, expansion, and transplantation, optimizing cell viability and functionality. This cell-based regenerative approach preserves Schlemm's canal 104 function rather than bypassing it, offering a more stable and physiological alternative to conventional glaucoma stents.

The present inventions relate to a bioengineered endothelial stent 118 for implantation in Schlemm's canal 104 to enhance aqueous fluid 204 outflow and restore physiological intraocular pressure regulation in patients with glaucoma. Unlike conventional glaucoma drainage devices, which provide unpredictable intraocular pressure-lowering effects due to variations in post-surgical healing and fibrosis, this novel endothelial stent 118 integrates transplanted Schlemm's canal endothelial cells 1402 (SCECs) to actively restore the natural function of the aqueous fluid 204 outflow pathway. The device consists of a biodegradable or biocompatible scaffold, engineered to conform to Schlemm's canal 104 dimensions, and a cell-seeding system that delivers and maintains functional endothelial cells 1402 along the inner walls 1514 of Schlemm's canal 104.

By promoting giant vacuole 1404 formation, transcellular pore development, and shear stress-responsive mechanotransduction, the endothelialized stent 118 enhances physiologic outflow resistance regulation, preventing excessive drainage while maintaining sustained intraocular pressure reduction. The inventions further include methods for endothelial cell 1402 isolation, expansion, and transplantation onto the endothelial stent 118 prior to or during implantation. This technology represents a shift in glaucoma treatment, leveraging tissue regeneration rather than passive fluid diversion, thereby offering predictable, long-term intraocular pressure control while preserving Schlemm's canal 104 function.

Described here is an endothelial-seeded stent 118 that functions to enhance aqueous fluid 204 flow while maintaining physiological resistance. The endothelial stent 118 combines mechanical support with active endothelial function to restore physiological aqueous fluid 204 outflow regulation. The endothelial stent 118 does not substantially interfere with transmural or circumferential flow within Schlemm's canal 104 and utilizes the natural drainage pathways of the eye. Excessive drainage of aqueous fluid 204 is prevented by modulating pore activity in response to pressure. The device has been developed in three primary embodiments that include nitinol, a bioabsorbable stent, and a hybrid stent. The hybrid embodiment stent 702 comprises a nitinol core with distal-only PLGA cladding configured to degrade over time while maintaining structural integrity. The endothelial stent 118 serves as a scaffold for drainage while encouraging migration, adhesion, and functional restoration of the endothelial cells 1402.

Unlike traditional minimally invasive glaucoma surgery (MIGS), the endothelial stent 118 implant does not just bypass resistance but replaces dysfunctional endothelial cells 1402 with a long-term biomimetic alternative to control intraocular pressure. Compared to stents prone to fibrosis, the synthetic endothelial implant reduces scarring and maintains function over time. Unlike regenerative approaches, which rely on fragile cell engraftment, the endothelial implant offers a stable, synthetic alternative with predictable outcomes.

shows the cornea 114 surrounding and enclosing the anterior chamber 110. The iris 112 is beneath the anterior chamber 110.

Figure 2:
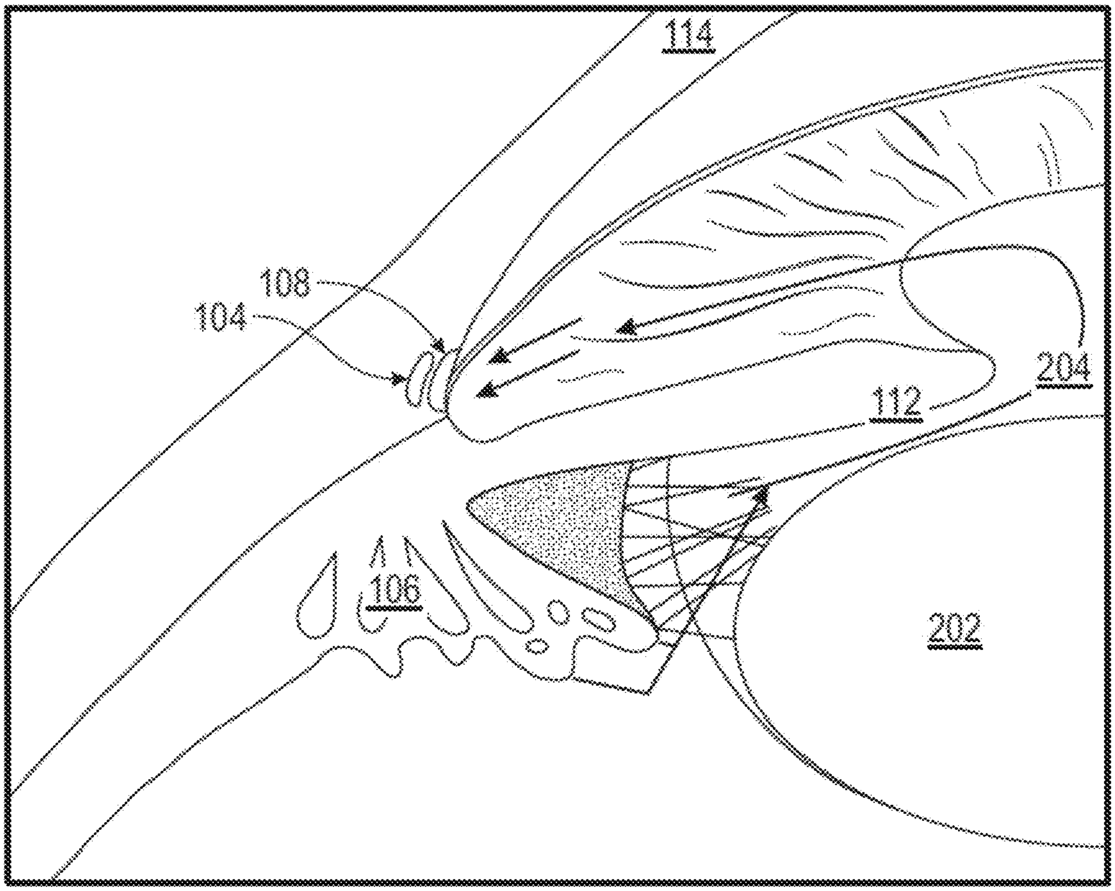
FIG. 2 is a diagram of the aqueous fluid flow in the eye.

FIG. 2 shows the flow of the aqueous fluid 204 in the eye 102. This is a detailed view showing the relationship of Schlemm's canal 104 and trabecular meshwork 108. The arrow shows the direction of aqueous fluid 204 flow between the iris 112 and the lens 202. In glaucoma, the most significant area of resistance to aqueous fluid 204 drainage from the eye 102 occurs at the interface between the trabecular meshwork 108 and the inner wall of Schlemm's canal 104.

Figure 3:
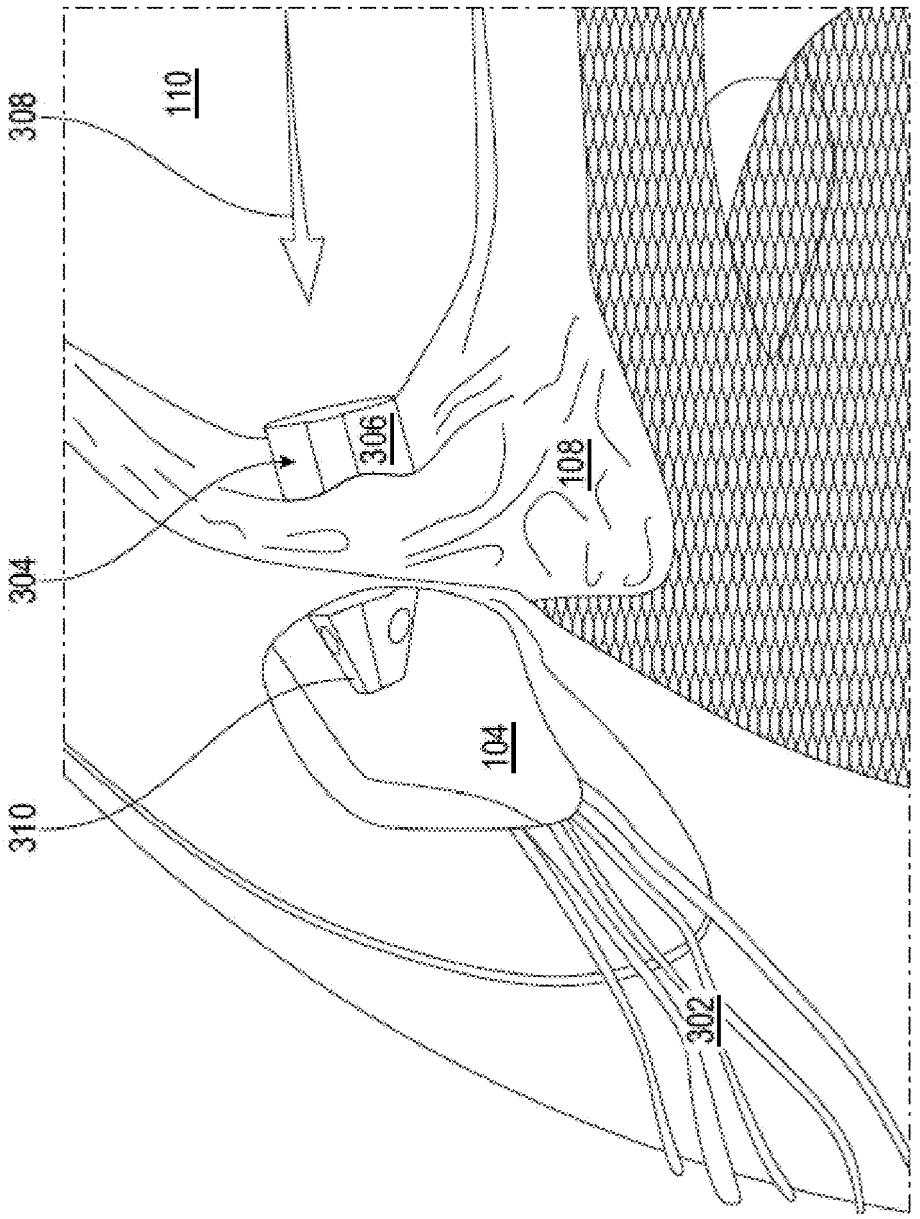
FIG. 3 illustrates a type of stent in the eye.

FIG. 3 is shows the eye with a type of stent 304 installed. This type of iStent attempts to overcome the resistance to aqueous fluid 204 flow by placing a bypass stent 304 that directs the aqueous fluid 204 from the anterior chamber 110 directly into Schlemm's canal 104. Of note is the collector channel 302 that directs the aqueous fluid 204 to blood vessels on the surface of the eye 102. The stent 304 has a stent head 306 that is wider than the distal end of stent 310. The stent head 306 has a lumen that allows the aqueous fluid flow 308 to pass into the distal end of stent 310, where it exits into Schlemm's canal 104.

TABLE 1

Summary of Stent Embodiments by Material, Coating, Degradation, and Clinical Use

| Stent Embodiment | Material | Coating | Degradation Profile | Clinical Use |
|---|---|---|---|---|
| Biodegradable Polymer Stent | PLLA (poly-L-lactic acid) | Anti-inflammatory peptide coating | Fully biodegradable (months) | Temporary support; facilitates endothelial regeneration |
| Hybrid Metal-Polymer Stent | Nitinol core + PLA shell | Bioactive ECM protein (e.g., fibronectin) | Partial degradation (polymer only) | Long-term mechanical integrity with surface bioactivity |
| Silicone Microstent | Medical-grade silicone | Uncoated or heparin-coated | Non-degradable | Permanent implant for chronic glaucoma |
| Hydrogel-Coated Titanium Stent | Titanium alloy | Hydrophilic hydrogel + VEGF | Non-degradable | Promotes cell adhesion, used in cases needing vascularization |
| Gelatin-Based Scaffold | Crosslinked gelatin | Laminin/Collagen coating | Rapid degradation (days-weeks) | Short-term implantation, enhances rapid endothelialization |
| Smart Polymer Stent | Thermoresponsive polymer | None or drug-eluting coating | Biodegradable or dissolvable | Self-expanding, used for minimally invasive insertion |
| Magnetically Guided Stent | Iron oxide-embedded PLA | Bioinert coating | Biodegradable (weeks-months) | Precision-guided placement; allows imaging and tracking |

Figure 4:
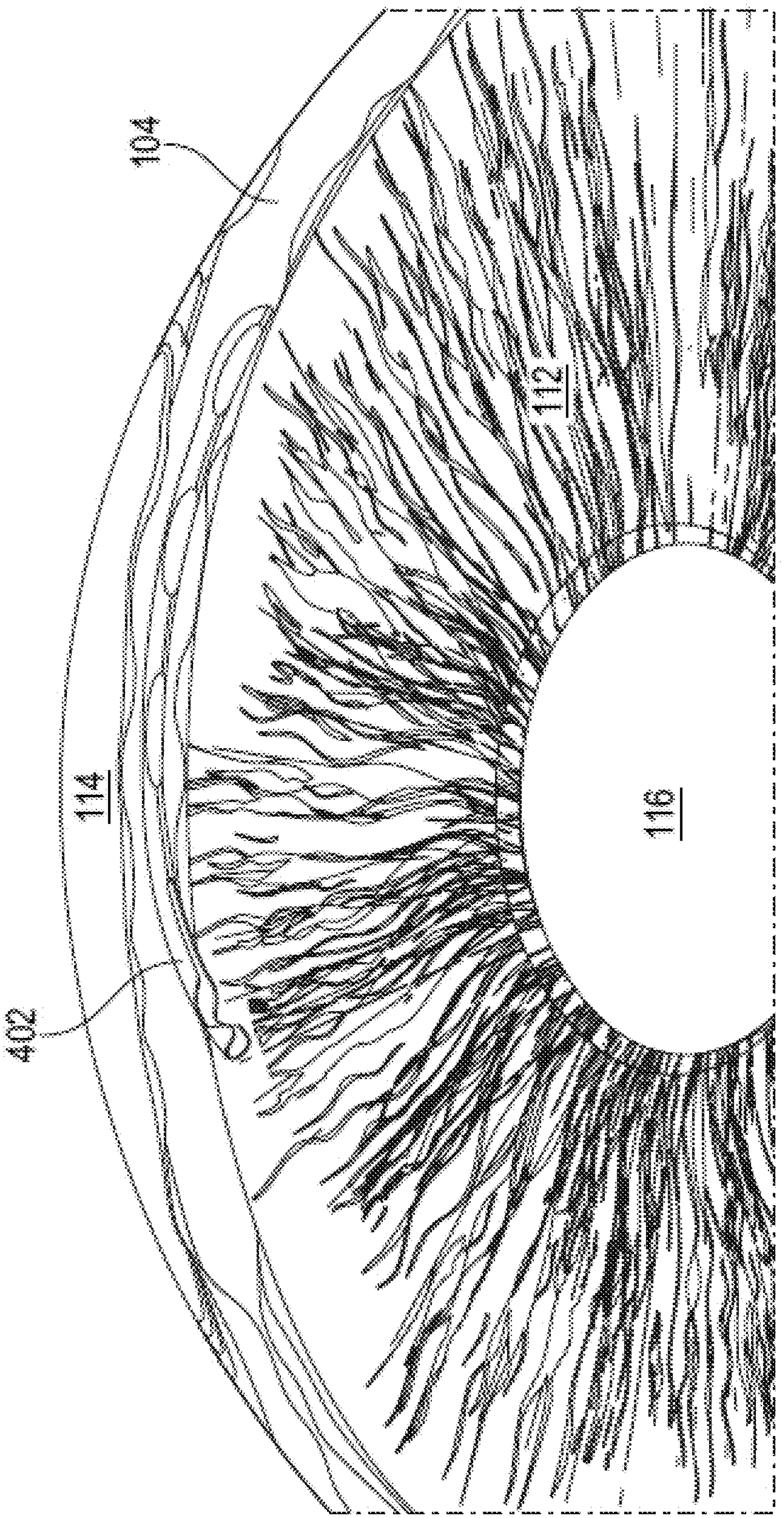
FIG. 4 illustrates another type of stent.

FIG. 1 shows the key anatomic landmarks in an eye 102. Clear fluid called aqueous fluid 204 is created in the ciliary body 106. Aqueous fluid 204 flows through the pupil 116 and into the anterior chamber 110. The aqueous fluid 204 leaves the eye 102 through the trabecular meshwork 108—a band of dark tissue around the base of the anterior chamber 110. The aqueous fluid 204 percolates through the trabecular meshwork 108 and into Schlemm's canal 104. The front of Schlemm's canal 104 is the back of the trabecular meshwork 108. The circumference of Schlemm's canal 104 is also 360 degrees. The back wall of Schlemm's canal 104 connects with collecting channels that direct the aqueous fluid 204 into blood vessels on the surface of the eye 102. FIG. 1 also FIG. 4 illustrates another type of Hydrus stent 402. This is an example of a stent (tube) that is inserted in Schlemm's canal 104 with a small terminal end extending out of Schlemm's canal 104 and into the anterior chamber 110. The Hydrus stent 402 attempts to bypass the trabecular meshwork 108 and direct aqueous fluid 204 into the Hydrus stent 402 within Schlemm's canal 104. The fenestrations of the Hydrus stent 402 are meant to facilitate the flow of aqueous fluid 204 throughout Schlemm's canal 104. The Hydrus stent 402 is placed into Schlemm's canal 104 by making an incision into the trabecular meshwork 108 by means of an introducer (similar to a simple syringe) with a pushing element.

Figure 5:
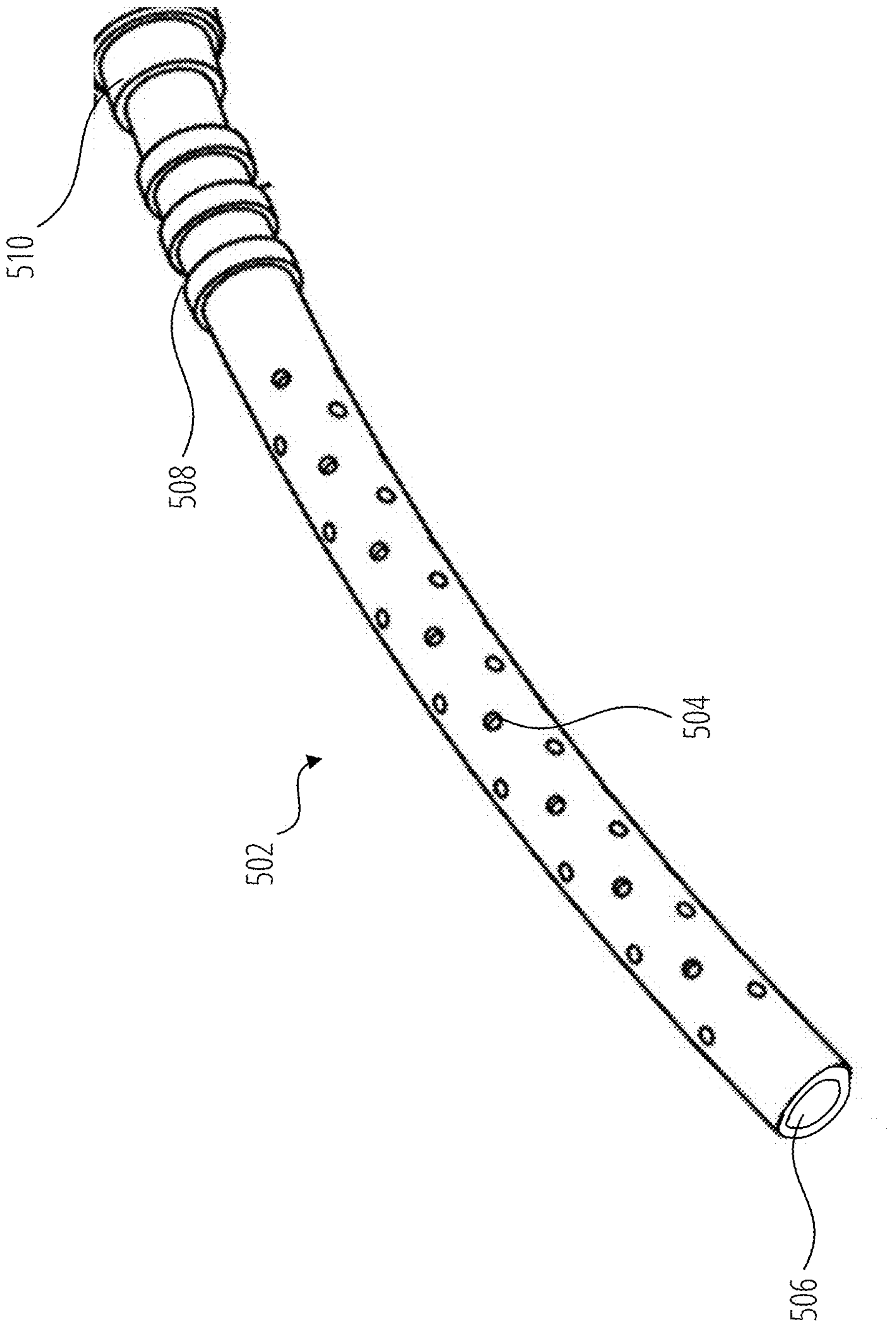
FIG. 5 illustrates a stent in one embodiment.

FIG. 5 shows one possible embodiment of a stent. This embodiment is designed to be inserted in Schlemm's canal 104 of the eye 102. The shape of this stent 502 is substantially cylindrical with a lengthwise curve to conform to the curvature of Schlemm's canal 104. In some embodiments, the stent 502 is straight, but made of flexible material that will conform to the curvature of Schlemm's canal 104 when inserted. The open lumen 506 is seen, an opening for allowing the aqueous fluid 204 to enter the stent 502 through the proximal collar 510 and exit the stent 502 via the micropores 504, putting the aqueous fluid 204 into Schlemm's canal 104. The lumen 506 may run the length of the stent 502. In some embodiments, the stent 502 could be made of collagen, hydrogels, or plastic such as a biodegradable polymer (poly(lactic-co-glycolic acid) (PLGA), polyethylene glycol (PEG), or polydimethylsiloxane (PDMS)). In some embodiments, the stent 502 has retention rings 508 to hold the stent 502 in Schlemm's canal 104.

Figure 6:
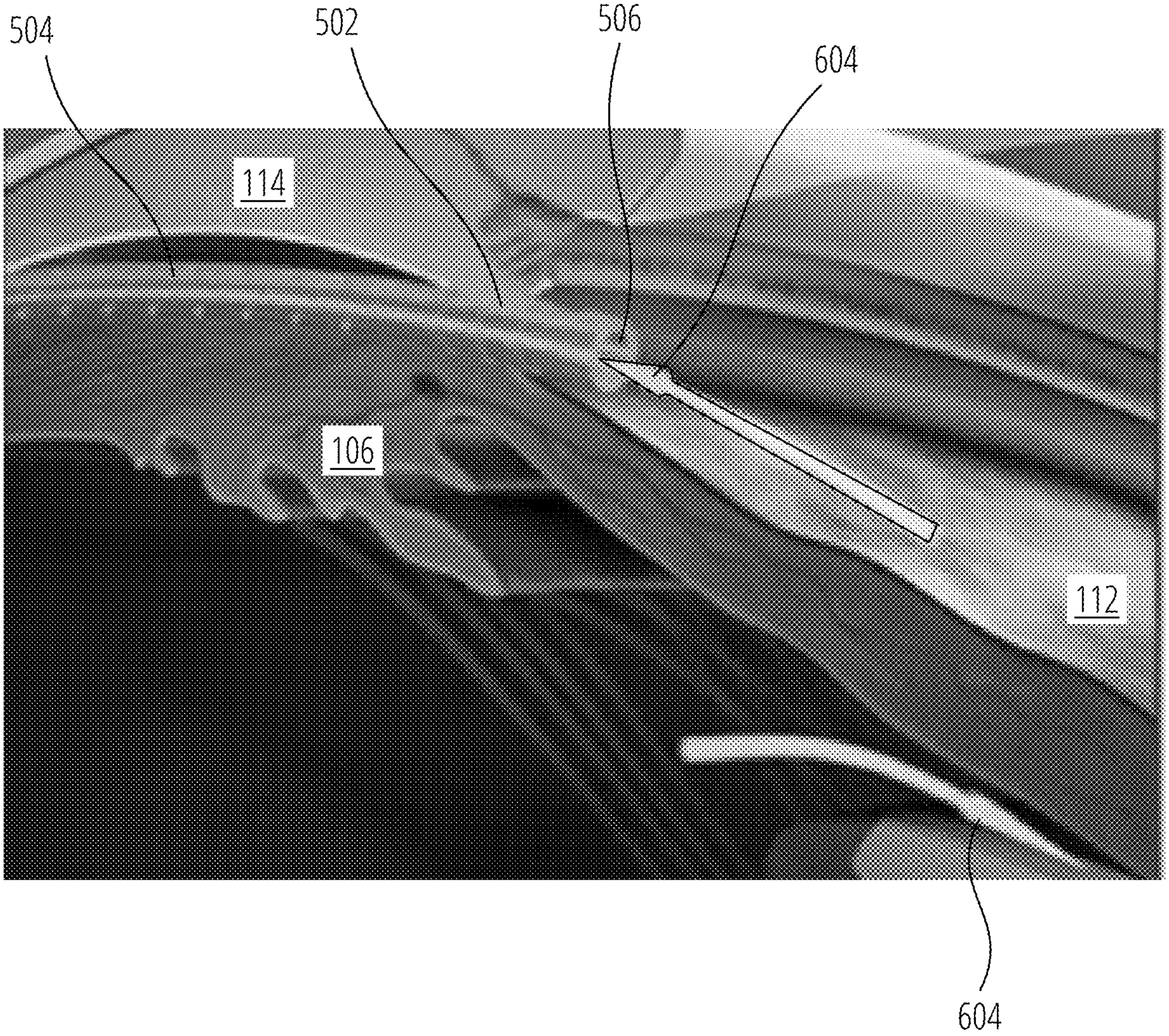
FIG. 6 shows the stent from FIG. 5 installed in the eye.

The stent 502 of FIG. 5 is seen inserted into the eye 102 in FIG. 6. The stent 502 is inserted into Schlemm's canal 104 between the ciliary body 106 and the cornea 114. The aqueous fluid 204 flows from the anterior chamber 110 into the lumen 506 of the stent 502 where it is dispersed through the micropores 504 into Schlemm's canal 104.

Partial or Fully Cladded Polymer Hybrid Embodiment

Figure 7:
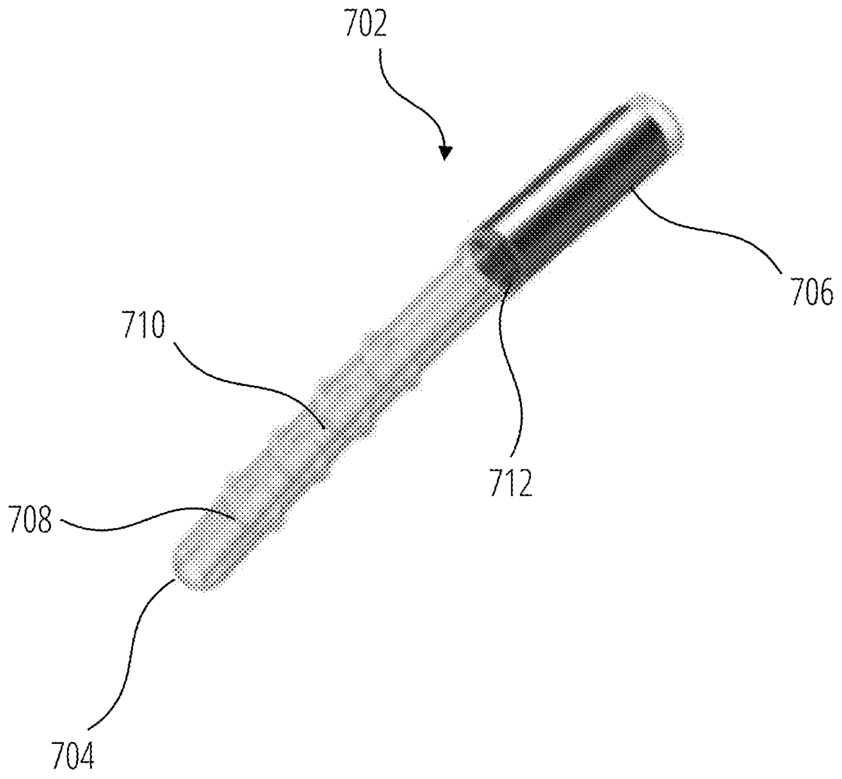
FIG. 7 is a perspective view of a hybrid stent 702 embodiment comprising a nitinol base segment that is partially clad with a distal polymeric coating. The polymer layer is configured to facilitate endothelial cell integration, while the exposed nitinol segment preserves structural integrity and ensures sustained patency within Schlemm's canal

FIG. 7 shows another embodiment of a stent 702. This embodiment is designed to be inserted into Schlemm's canal 104 of the eye 102. This hybrid stent 702 embodiment comprises a core structure—typically composed of self-expanding nitinol 706—for mechanical support and conformability within Schlemm's canal 104. A partial or full outer coating of biodegradable polymer is applied to the tip or select regions of the stent 702. This coating is designed to degrade over time, enabling endothelial cell 1402 migration, adhesion, and functional integration onto the stent 702 surface, while maintaining structural patency and regulated aqueous outflow during the integration period As shown in FIG. 7, the hybrid stent 702 comprises a nitinol core 706 and a polymer coating 710 that may be applied either partially (e.g., to the distal region) or fully over the stent's exterior. This hybrid configuration provides mechanical stability through the self-expanding nitinol core while offering a bioresorbable interface that facilitates endothelial cell 1402 migration and integration. The transitional interface 712 may include spatially graded changes in stiffness or permeability to promote functional tissue interaction and controlled biodegradation.

The shape of this stent 702 is substantially cylindrical with a lengthwise curve meant to conform to the curvature of Schlemm's canal 104. The lumen 704 may run the length of the stent 702. The open lumen 704 allows the aqueous fluid 204 to enter the stent 702 and exit the stent 702 via the exposed nitinol proximal segment 706 (which could have micropores), putting the aqueous fluid 204 into Schlemm's canal 104. In some embodiments, the stent 502 could be made of Polyethersulfone (PES) and titanium, collagen, hydrogels, or plastic such as a biodegradable polymer (poly (lactic-co-glycolic acid) (PLGA), polyethylene glycol (PEG), or polydimethylsiloxane (PDMS)). In some embodiments, the stent 702 has a Polymer-coated distal region 710 that may have one or more rings 708 to hold the stent 702 in Schlemm's canal 104. A transitional interface 712 may be located between the exposed nitinol proximal segment 706 and the Polymer-coated distal region 710.

Figure 8:
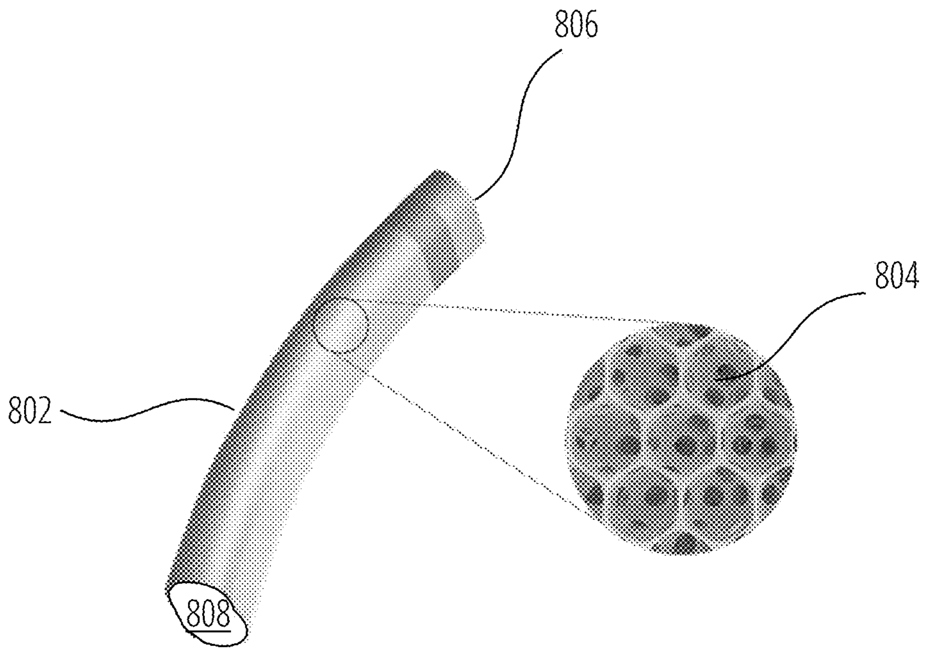
FIG. 8 illustrates a stent in a third embodiment.
Figure 9:
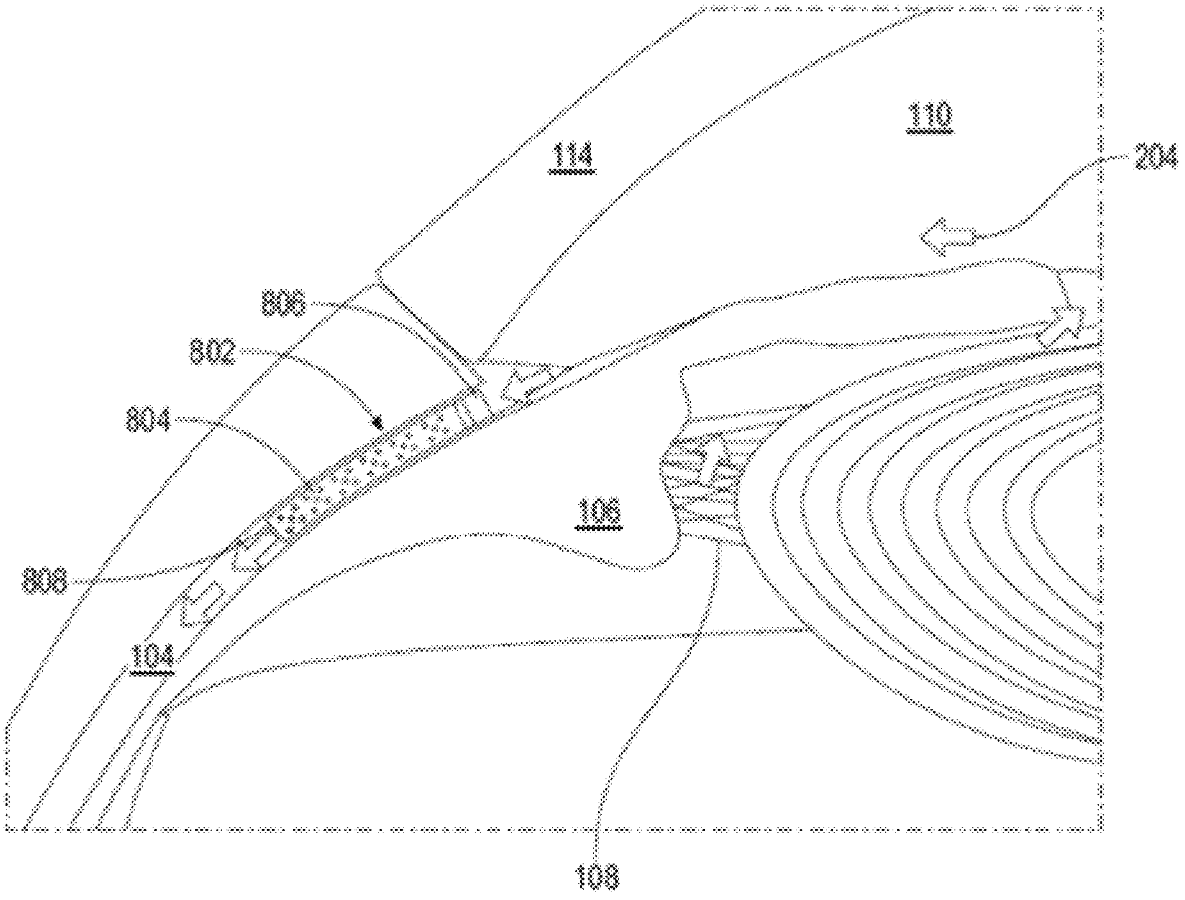
FIG. 9 shows the stent from FIG. 8 installed in the eye.

FIG. 8 is a third embodiment of a stent 802. This stent 802 is also designed to be embedded in Schlemm's canal 104 as seen in FIG. 9. The shape of this stent 802 is substantially cylindrical with a lengthwise curve meant to conform to the curvature of Schlemm's canal 104. In some embodiments, the stent 802 has no lengthwise curve but is made of flexible material that will conform to the curvature of Schlemm's canal 104. The open stent end 806 allows the aqueous fluid 204 to enter the stent 802 and exit the stent 802 via the micropores 804 and the distal lumen 808, putting the aqueous fluid 204 into Schlemm's canal 104. In some embodiments, the distal lumen 808 could be closed.

In some embodiments, the stent 802 could be made of silicone or a biocompatible polymer, such as synthetic polymers, naturally-occurring polymers, or mixtures thereof. Exemplary synthetic biocompatible polymers include, but are not limited to, poly(2-hydroxyethyl methacrylate), silicone rubber, poly(ε-caprolactone) dimethylacrylate, polysulphone, poly(methyl methacrylate) (PMMA), fluoropolymers (such as Teflon), polyethylene tetraphthalate (PET or Dacron), polyamide (such as Nylon), polyvinyl alcohol, polyurethane, interpenetrating network polymers, and mixtures thereof. Exemplary naturally-occurring biocompatible polymers include, but are not limited to, fibrous or globular proteins, complex carbohydrates, glycosaminoglycans, or mixtures thereof. Thus, the polymer scaffold may include collagens of all types, elastin, hyaluronic acid, alginic acid, desmin, versican, matricelluar proteins such as SPARC (osteonectin), osteopontin, thrombospondin 1 and 2, fibrin, fibronectin, vitronectin, albumin, etc.

Alternately, a hydrogel could be used as a material, for example, a degradable hydrogel, which is formed by reacting low-molecular-weight poly(ε-caprolactone) diol with an excess of methacryloyl chloride to give a polyester compound with methacrylate endgroups, the polyester compound being copolymerised with 2-hydroxyethyl methacrylate (HEMA) to yield a cross-linked hydrogel with hydrolysable linkages. Note that these materials could be used for any of the stents 502, 702, 304, 402, 1002 described herein.

The stent 802 in the hydrogel embodiment may not have a lumen; instead, the micropores 804 may allow the aqueous fluid 204 to flow from the stent end 806 through the stent 802 via the holes between the pores.

TABLE 2

Time-Based Hydrogel Degradation.

| Stage | Time | Appearance |
|---|---|---|
| 1 | Day 0 (Implantation) | Hydrogel completely covers stent, endothelial cells protected. |
| 2 | Day 3-5 | Small breaks in hydrogel layer, initial cell exposure begins. |
| 3 | Day 7-10 | Hydrogel 50% dissolved, endothelial cells migrating into Schlemm's canal. |
| 4 | Day 14+ | Hydrogel completely degraded, leaving fully endothelialized stent. |

In FIG. 9, the stent 802 is inserted between the ciliary body 106 and the cornea 114 into Schlemm's canal 104. The aqueous fluid 204 is created in the trabecular meshwork 108 and flows into the anterior chamber 110. From the anterior chamber 110, the aqueous fluid 204 enters the stent 802 at the stent end 806 and may pass through the micropores 804 down the length of the stent 802 and into Schlemm's canal 104.

Figure 10:
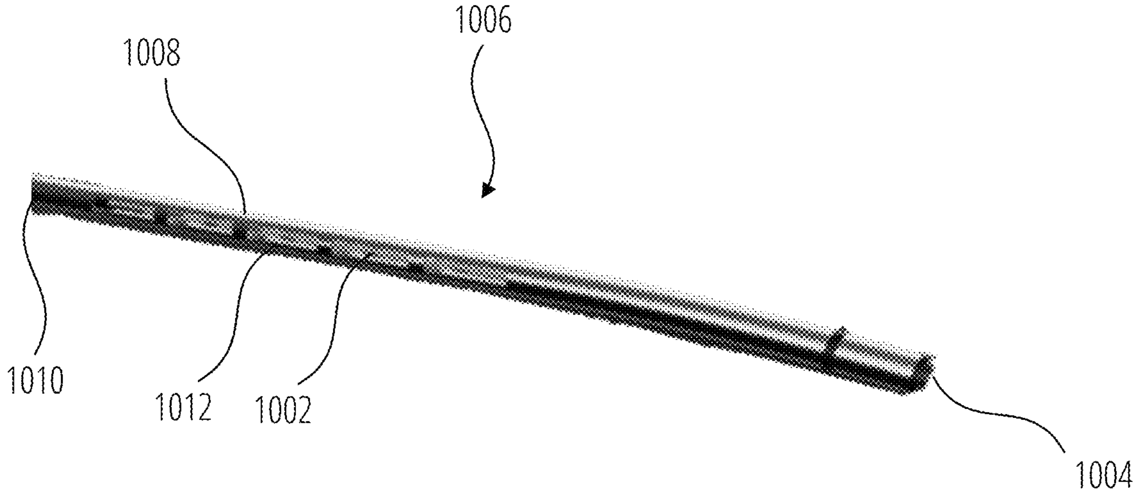
FIG. 10 is a partial cutaway view illustrating an introducer for delivery of a fenestrated stent into Schlemm's canal.

FIG. 10 illustrates a stent 1002, such as a Hydrus™ stent, positioned within a delivery introducer 1006. A portion of the introducer 1006 is cut away 1008 to reveal the stent 1002 nested within the lumen 1004 of the introducer 1006. The introducer 1006 is designed to insert the stent 1002 into Schlemm's canal 104 of the eye 102. The introducer 1006 includes a proximal tip or trochar 1010, which can be configured to create an incision in the trabecular meshwork 108 to access Schlemm's canal 104, and allow guided advancement of the stent 1002.

The lumen 1004 of the introducer 1006 runs the entire length of the device and houses the stent 1002 during delivery. The stent 1002 has a curved, substantially cylindrical shape that conforms to the natural arc of Schlemm's canal 104. The stent 1002 includes multiple micropores or fenestrations 1012, shown here as rectangular openings along its wall, which are configured to permit aqueous fluid 204 to flow through the lumen 1004 and into Schlemm's canal 104. Following deployment of the stent 1002, it remains within Schlemm's canal 104 while the introducer 1006 is withdrawn.

In this embodiment, the stent 1002 is designed to be inserted in Schlemm's canal 104 of the eye 102. The shape of this stent 1002 is substantially cylindrical with a lengthwise curve meant to conform to the curvature of Schlemm's canal 104. The lumen 1004 may run the length of the stent 1002. The open lumen 1004 allows the aqueous fluid 204 to enter the stent 1002 and exit the stent 1002 via the multiple micropores or fenestrations 1012, putting the aqueous fluid 204 into Schlemm's canal 104.

Figure 11:
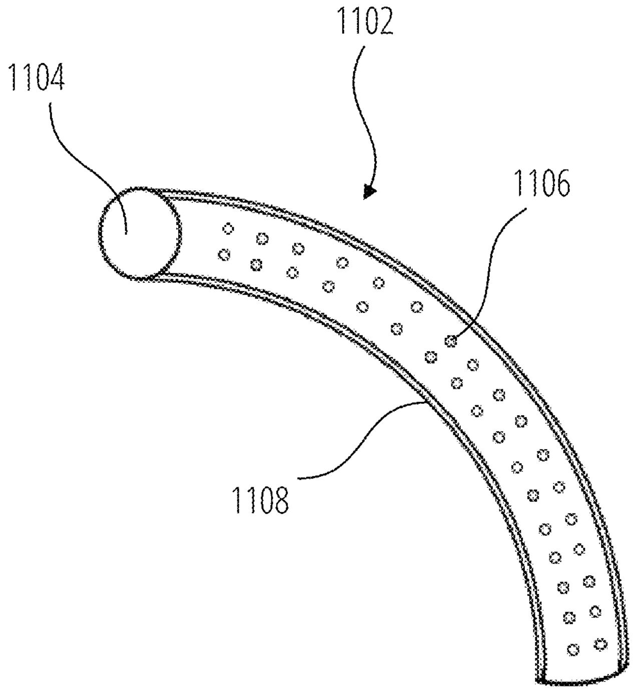
FIG. 11 is a line drawing of a fifth embodiment of the stent.

FIG. 11 shows another embodiment of the stent 1102. In this embodiment, the stent 1102 has an open lumen 1104 to allow aqueous fluid 204 to enter the stent 1102 from the anterior chamber 110 when the stent 1102 is installed in Schlemm's canal 104. Micropores 1106 are distributed along the length of the stent 1102, allowing the aqueous fluid 204 to enter Schlemm's canal 104. In some embodiments, a hydrogel coating 1108 covers the stent 1102. The stent 1102 could be made of Polyethersulfone (PES) and titanium, collagen, hydrogels, or plastic such as a biodegradable polymer (poly(lactic-co-glycolic acid) (PLGA), polyethylene glycol (PEG), or polydimethylsiloxane (PDMS)). In other embodiments, the stent 1102 could be made of silicone or a biocompatible polymer, such as synthetic polymers, naturally-occurring polymers, or mixtures thereof. Exemplary synthetic biocompatible polymers include, but are not limited to, poly(2-hydroxyethyl methacrylate), silicone rubber, poly(ε-caprolactone) dimethylacrylate, polysulphone, poly(methyl methacrylate) (PMMA), fluoropolymers (such as Teflon), polyethylene tetraphthalate (PET or Dacron), polyamide (such as Nylon), polyvinyl alcohol, polyurethane, interpenetrating network polymers, and mixtures thereof. Exemplary naturally-occurring biocompatible polymers include, but are not limited to, fibrous or globular proteins, complex carbohydrates, glycosaminoglycans, or mixtures thereof. Thus, the polymer scaffold may include collagens of all types, elastin, hyaluronic acid, alginic acid, desmin, versican, matricelluar proteins such as SPARC (osteonectin), osteopontin, thrombospondin 1 and 2, fibrin, fibronectin, vitronectin, albumin, etc. Alternately, a hydrogel could be used as a material, for example, a degradable hydrogel, which is formed by reacting low-molecular-weight poly(ε-caprolactone) diol with an excess of methacryloyl chloride to give a polyester compound with methacrylate endgroups, the polyester compound being copolymerised with 2-hydroxyethyl methacrylate (HEMA) to yield a cross-linked hydrogel with hydrolysable linkages. The hydrogel coating 1108 described herein may be adapted for endothelial reseeding within Schlemm's canal 104.

The present inventions relate to an endothelial cell-seeded stent 118 designed for implantation in Schlemm's canal 104 to restore physiological regulation of aqueous fluid 204 outflow. Each stent embodiment comprises a microporous scaffold, which may be biocompatible, bioabsorbable, or a hybrid construction incorporating both features. In the hybrid embodiments (e.g., stent 702), the stent 702 includes a nitinol core for mechanical stability and a polymer cladding that may be applied fully or partially to its surface to enable controlled biodegradation and facilitate endothelial integration. These stents 702 are engineered to integrate with the endothelium of Schlemm's canal 104, supporting mechanotransduction and dynamic resistance to aqueous fluid 204 outflow. Unlike traditional trabecular meshwork bypass stents, the disclosed devices promote physiologic resistance modulation, prevent excess drainage, and enable sustained, predictable long-term intraocular pressure control.

The endothelial stent 118 is configured to conform to Schlemm's canal 104 dimensions, with a length determined by its embodiment, material composition, and intended purpose. The device is designed to fit within Schlemm's canal 104, which has an average diameter of 190 to 350 microns.

The endothelial stent 118 is intended to be sufficiently long to engage with multiple collector channel 302 openings, but not so long that it obstructs the flow of aqueous fluid 204 within Schlemm's canal 104.

In general, the length of the endothelial stents 118, including all embodiments, may range from approximately 2 mm to 20 mm. Segmental stents, configured as multiple linked units within Schlemm's canal 104, may have individual segments measuring between 2 mm and 15 mm. The endothelial stents 118 may be manufactured at lengths sufficient to span a desired segment or even the full 360-degree circumference of Schlemm's canal 104, which measures approximately 40 mm.

The cross-sectional thickness of the endothelial stents 118—measured from the inner lumen to the outer surface—may range from 50 microns to 500 microns, depending on the material and embodiment. In the nitinol-based embodiment, axial thickness may range from 50 to 150 microns. The bioabsorbable embodiments composed of materials such as poly(lactic-co-glycolic acid) (PLGA) or polyethylene glycol (PEG) may have axial thicknesses between 150 and 250 microns. The hybrid embodiments, such as stent 702, incorporate a nitinol core for structural support and may feature a polymer coating applied either fully or partially along the length of the device; these hybrid designs may have axial thicknesses ranging from 150 to 300 microns, accommodating both mechanical performance and localized biointegration.

The lumen 506, 704, 1104 of the endothelial stent 118 serves as a conduit for aqueous fluid 204, while the exterior surface of the endothelial stent 118 is designed for endothelial cell 1402 adhesion and integration. The device can incorporate micropores 504, 706, 804, 1106 in the wall of the endothelial stent 118 that are strategically positioned to facilitate transmural flow and pressure-responsive outflow while maintaining mechanical strength. The micropores 504, 706, 804, 1106 could be 0.5 to 1 micron in diameter and may be incorporated in the full-thickness in the wall. The pluralities of micropores 504, 706, 804, 1106 are situated in a longitudinal direction along its axis.

Endothelial-Stent Surface Embodiments

The design of the endothelial stent 118 or delivery system—such as surface roughness, chemical modifications, or microstructures intended to enhance adhesion—can influence the effective density of required endothelial cells 1402. Surface modifications that promote rapid and robust cell attachment may allow for lower seeding densities, while less interactive surfaces might require a higher density to achieve confluence.

Alterations of the surface can also influence the migration of endothelial cells 1402 from the endothelial stent 118 to the adjacent walls of Schlemm's canal 104. Incorporating biodegradable polymer coatings that release bioactive agents (e.g., anti-inflammatory drugs, pro-endothelialization factors) over time can help create a more favorable microenvironment for cell survival and integration. Such drug-eluting coatings may serve as temporary scaffolds that gradually degrade as the newly formed endothelial layer matures.

In some embodiments, the endothelial-seeded stent 118 can be enhanced with the addition of mural cells, including pericytes and smooth muscle-like cells. In Schlemm's canal 104, mural cells regulate vessel tone, endothelial permeability, and mechanotransduction, which are important for aqueous fluid 204 outflow and intraocular pressure homeostasis.

Unlike blood vessels that have a continuous layer of mural cells, Schlemm's canal 104 has an incomplete layer, supporting segmental aqueous fluid 204 flow. Mural cells support intraocular pressure control by influencing transcellular pore formation and shear stress responses in endothelial cells 1402, thus modulating outflow resistance. Inclusion of mural cells in the bioengineered stent supports endothelial adhesion to the wall of Schlemm's canal 104.

Mural cells facilitate endothelial migration from the endothelial stent 118 to the native canal resulting in quicker recovery time and decreased likelihood of incomplete endothelialization along the endothelial stent 118 and Schlemm's canal 104 walls. Fibrotic changes involving endothelial cells that impair outflow over time can be prevented by platelet-derived growth factor (PDGF-BB) that is produced by mural cells.

For long-term stability, outflow regulation, consistent control of intraocular pressure, and prevention of fibrosis, viable mural cells incorporated on the endothelial stent 118 are important. Otherwise, stent coatings with PDGF-BB or bioactive ECM proteins may be needed to compensate for their absence.

General Stent Structure

In one embodiment, the endothelial stent 118 comprises a curved tubular or semi-flexible structure having a lumen 506, 704, 1004 extending longitudinally along its axis. The radius of curvature may range from approximately 4 to 9 mm to conform to the curvature of Schlemm's canal 104. The outer surface of the endothelial stent 118 is seeded with a monolayer of Schlemm's canal endothelial cells 1402, forming a biologically active interface with the native canal lining. The scaffold may be fabricated from biocompatible metals (e.g., nitinol), biodegradable polymers (e.g., PLGA, PEG), or a hybrid combination of both, such as a nitinol core with a full or partial polymer cladding designed to support endothelial migration and integration.

The external surface of the endothelial stent 118 may be microstructured or chemically treated to enhance endothelial cell 1402 adhesion. For example, micro-roughening or nanopatterning of the polymer or metal surfaces may improve endothelial cell 1402 anchoring and viability. In the hybrid stent embodiments 702, 802, the polymer coating may be applied selectively to the distal end, circumferentially, or along targeted regions to promote a favorable biological response while preserving canal patency through mechanical support from the underlying metallic core.

Material Variations

The endothelial stent 118 is composed of biocompatible materials that include collagen, hydrogels, or bioengineered polymers e.g., PEG, PLGA, or PDMS) that support cell adhesion and viability. Porous or micropatterned surfaces allow cell attachment and nutrient flow. The endothelial stent 118 substantially matches the shape and curvature of Schlemm's canal 104 to ensure proper mechanical and biological integration.

Stent Fabrication and Design Features

Nitinol Stent Embodiment (Metallic Self-Expanding Design)

In one embodiment, the endothelial stent 118 is composed of a shape-memory alloy such as nitinol (NiTi), allowing it to self-expand upon implantation and conform to the curvature of Schlemm's canal 104. The self-expanding property ensures consistent contact with the internal wall of Schlemm's canal 104. The endothelial stent 118 can be composed of other titanium alloys, including Ti-6Al-4V. The nitinol valve can have a variety of individual or combined coatings, including microporous titanium oxide surface to promote endothelial adhesion, plasma-treated hydrophilic coating to enhance aqueous fluid 204 interaction, and a nitric oxide-releasing polymer to prevent fibrosis and inflammation.

The nitinol endothelial stent 118 is well-suited for long-term implantation because it keeps Schlemm's canal 104 open while the endothelial layer helps control fluid drainage naturally. The nitinol stent is preferred in patients with moderate to severe glaucoma requiring long-term structural support or in patients with extensive trabecular meshwork 108 fibrosis who may benefit from a permanent scaffold.

Drug-Eluting and ECM Coating Options

In certain embodiments, the nitinol scaffold may be partially or fully coated or clad with a biodegradable polymer layer. Partial coating or cladding may be used to target specific regions, such as the distal tip, for enhanced endothelialization, while allowing the remainder of the scaffold to provide long-term mechanical support. This selective application may also serve to control the release of bioactive compounds embedded within the polymer, such as extracellular matrix (ECM) proteins, vascular endothelial growth factor (VEGF), or nitric oxide (NO)-releasing agents. Upon degradation, the exposed nitinol surface continues to provide structural stability, reducing the risk of fibrosis or device migration."

Bioabsorbable Stent Embodiment (Degradable Scaffold for Endothelial Integration)

In another embodiment, the endothelial stent 118 is composed of a biodegradable polymer scaffold, designed to gradually degrade over 1 to 6 months, allowing native Schlemm's canal 104 endothelial cells 1402 to replace it.

The composition of the bioabsorbable endothelial stent 118 can consist of one or a combination of materials that includes poly(lactic-co-glycolic acid) (PLGA), polyethylene glycol (PEG) hydrogel, and polydimethylsilaxane (PDMS) microstructures. VEGF (Vascular Endothelial Growth Factor) and ECM (Extracellular Matrix) adhesion proteins can be incorporated into the endothelial stent 118 through coatings, embedding within the polymer matrix, or surface modifications, to avoid chronic inflammation and fibrosis.

The bioabsorbable endothelial stent 118 gradually resorbs, leaving behind a functional endothelialized outflow pathway. The bioabsorbable endothelial stent 118 supports native migration and proliferation of endothelial cells 1402.

This embodiment is suited for patients with mild-to-moderate glaucoma where temporary mechanical support is needed, but long-term retention of a permanent device is unnecessary. Individuals with severe Schlemm's canal 104 fibrosis are not ideal candidates for a temporary scaffold. Table 3 showing degradation rates by material.

TABLE 3

Degradation Rates by Material

| Material | Degradation Time | Comments |
|---|---|---|
| PLGA (50:50 Lactic/Glycolic Acid) | 1-3 months | Fastest degrading formulation, optimal for temporary scaffolds. |
| PLGA (75:25 Lactic/Glycolic Acid) | 3-6 months | Slower degradation for longer endothelial support. |
| PLGA (85:15 Lactic/Glycolic Acid) | 6-12 months | Used in hybrid designs, allows gradual transition to native function. |
| PEG Hydrogel (Cross-linked) | Weeks to ~3 months | Rapid degradation, useful for lubricious coatings. |
| Polydimethylsiloxane (PDMS) Microstructures | 6-18 months | Longer stability, maintains micropore integrity. |
| Hybrid Nitinol Core + PLGA Coating | Coating: 3-6 months | Permanent nitinol support, with bioabsorbable layer promoting endothelialization. |

Hybrid Endothelial Stent Embodiment with Nitinol Core and Full or Partial Polymer Cladding (Dual-Layer Composite Design)

In another embodiment, the hybrid endothelial stent 702 comprises a nitinol support core that is fully or partially clad with a biodegradable polymer coating. This dual-layer composite design provides immediate mechanical support from the nitinol core, while the bioabsorbable cladding promotes gradual endothelialization as it degrades. This structure facilitates controlled shear stress distribution to enhance endothelial cell 1402 function. The nitinol framework ensures sustained patency of the stent 702, while the outer polymer layer gradually resorbs over a period of 2 to 6 months, enabling endothelial cell 1402 integration and reducing the risk of fibrosis at the nitinol-polymer interface. Optionally, the bioabsorbable coating may incorporate extracellular matrix (ECM) proteins such as fibronectin or laminin, and growth factors such as VEGF, to further promote endothelial cell migration and adhesion.

This embodiment is ideally suited for patients requiring an immediate stenting effect with long-term endothelialization benefits, combining the durability of nitinol with the regenerative potential of bioabsorbable materials.

Micropore Structure & Fluid Flow Control

The endothelial stent 118 may feature micropores 504, 804, 1106 with a diameter of 0.5 to 2 microns, strategically positioned to facilitate aqueous humor outflow, to ensure uniform shear stress distribution, and replicate the filtration function of Schlemm's canal.

In one embodiment, the micropores 504, 804, 1106 are evenly distributed along the outer surface, allowing for consistent transmural and circumferential aqueous humor circulation while preventing localized high-flow areas. Alternatively, in another embodiment, micropores are asymmetrically positioned to direct outflow toward specific collector channel openings.

Figure 16:
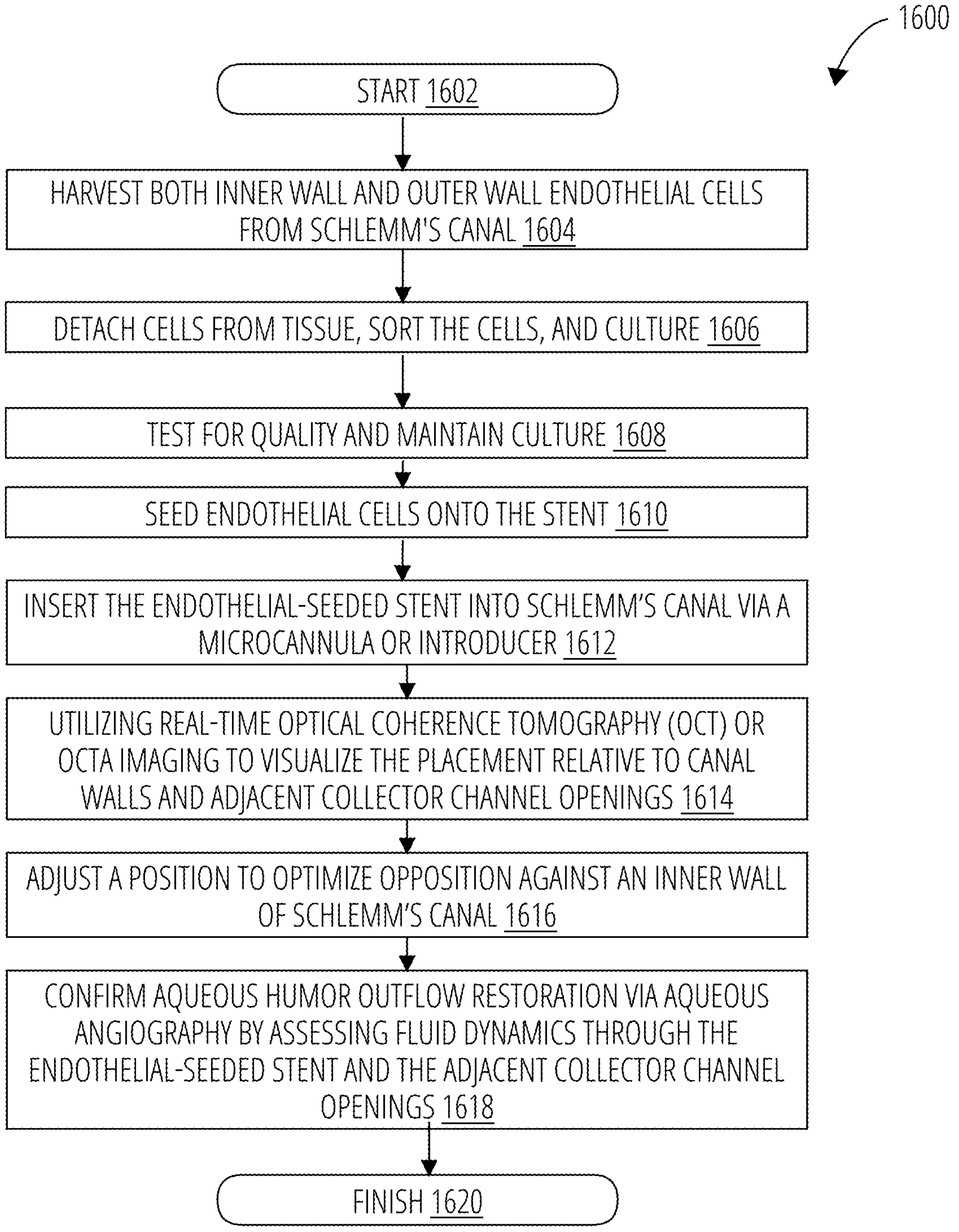
FIG. 16 illustrates a routine 1600 for guiding and verifying placement of an endothelial-seeded stent in Schlemm's canal, in accordance with one embodiment.

Harvesting and Handling of Schlemm's Canal Endothelial Cells for Stent Seeding The successful transplantation of Schlemm's canal 104 endothelial cells 1402 (SCECs) onto an implantable endothelial stent 118 relies on the ability to efficiently harvest, isolate, expand, and preserve viable endothelial cells 1402 while maintaining their specialized function. Schlemm's canal 104 endothelial cells 1402 play a fundamental role in regulating aqueous fluid 204 outflow and maintaining intraocular pressure, and their dysfunction is a key factor in glaucoma progression. See FIG. 16 for a flowchart of the seeding of an endothelial stent 118, starting at block start 1602.

Given the delicate nature of Schlemm's canal 104 and the relatively small endothelial cell 1402 population, obtaining viable SCECs from cadaveric donor tissue presents technical challenges that should be addressed to ensure a viable cell population for therapeutic applications. The isolation process should ensure high cell viability and functional integrity, enabling the transplanted cells to integrate with native tissue and restore physiological outflow resistance. Several methods have been developed to address these challenges, adapting techniques from research applications for potential therapeutic use.

An approach for isolating Schlemm's canal 104 endothelial cells 1402 involves precise microdissection of the anterior segment of cadaveric donor eyes. Under a stereomicroscope, the trabecular meshwork 108 and Schlemm's canal 104 are carefully identified, and fine microsurgical instruments are used to isolate the Schlemm's canal 104 inner wall 1514 endothelial cells 1402. This is challenging because it has a fragile and narrow structure, and may require a high degree of technical skill.

Schlemm's canal 104, which contains the specialized endothelial layer responsible for regulating outflow resistance. This method allows for direct visualization of Schlemm's canal 104 endothelium, ensuring precise isolation of the target tissue while minimizing contamination from adjacent structures. Inner wall 1514 and outer wall 1512 endothelial cells 1402 from Schlemm's canal 104 exhibit phenotype plasticity in response to environmental cues that include substrate stiffness, shear stress, and biochemical signals. Therefore, segregation of each type of endothelial cell is not necessary in many situations. See block 1604.

To increase the number of viable endothelial cells 1402 available for endothelial stent 118 seeding, enzymatic digestion is often employed following microdissection. The excised Schlemm's canal 104 tissue is treated with collagenase, dispase, or trypsin, which break down the extracellular matrix (ECM) and loosen cell-cell junctions, allowing endothelial cells 1402 to detach from the tissue. The effectiveness of this method depends on precise control of enzyme concentration and incubation time, as excessive exposure can compromise cell membrane integrity and mechanosensitive properties. When properly optimized, enzymatic digestion provides a higher yield of viable endothelial cell 1402 compared to mechanical dissection alone while preserving their functional characteristics for transplantation.

Following isolation, cell sorting and culture techniques ensure that only Schlemm's canal 104 endothelial cells 1402 are expanded and prepared for endothelial stent 118 seeding. The initial cell suspension is filtered and centrifuged, removing debris and non-endothelial contaminants before the cells are plated onto extracellular matrix (ECM)-coated culture dishes to promote attachment and proliferation. In some cases, fluorescence-activated cell sorting (FACS) is used to enrich the population of Schlemm's canal 104 endothelial cells 1402, selecting for markers such as CD31 (PECAM-1), which is associated with endothelial identity, VE-cadherin, which is crucial for cell-cell adhesion, and Schlemm's canal-specific markers such as PROX1, TEK, or FOXC2. Because Schlemm's canal 104 endothelial cells 1402 are highly mechanosensitive, maintaining them under shear stress conditions in a bioreactor system may be necessary to preserve their physiological function before transplantation. See block 1606.

Once the endothelial cells 1402 have been successfully expanded and characterized, they are subjected to rigorous quality control testing before being prepared for clinical use. This includes viability assays to confirm cell survival rates, morphological assessment under phase-contrast microscopy, and functional testing, such as permeability assays, to ensure that the cells retain their natural barrier properties and transcellular pore function. Healthy endothelial cells 1402 typically exhibit a cobblestone appearance in culture. Additionally, endotoxin and sterility testing are conducted to eliminate the risk of microbial contamination. See block 1608.

For short-term storage, endothelial cells 1402 may be maintained in low-serum or serum-free endothelial cell media within standard tissue culture plates or suspension culture vials at 4° C. to 8° C. for transportation. If the endothelial cells 1402 require longer-term storage, they may be cryopreserved in dimethyl sulfoxide (DMSO)-containing freezing media and stored in liquid nitrogen, although thawing protocols should be optimized to maintain viability.

Prior to delivery to the surgeon, the endothelial cells 1402 may be pre-seeded onto the endothelial stent 118 in a controlled bioreactor environment, allowing the endothelial cells 1402 to adhere and adapt to shear stress conditions before implantation. Alternatively, endothelial cells 1402 may be delivered in a suspension format within sterile, pre-filled vials, which the surgeon can use to apply the endothelial cells 1402 directly onto the endothelial stent 118 immediately before implantation. In either case, specialized transport packaging is used to ensure that the endothelial cell 1402 maintain viability during transit to the surgical facility. See block 1610.

Harvesting Schlemm's canal 104 endothelial cells 1402 for regenerative therapies may require a balance between precision, yield, and functional preservation. While microdissection provides direct, high-purity isolation, enzymatic digestion enhances cell yield while maintaining viability. Once isolated, cell sorting and culture techniques allow for the expansion and enrichment of Schlemm's canal 104 endothelial cells 1402, ensuring that they retain their physiological properties before implantation. The combination of these methods establishes a scalable and viable strategy for restoring Schlemm's canal 104 function, offering a regenerative approach to glaucoma treatment that integrates mechanosensitive endothelial therapy with bioengineered stent technology.

A further embodiment includes a dual-layer seeding technique, wherein endothelial progenitor cells (EPCs) or Schlemm's canal 104 endothelial cells 1402 (SCECs) are selectively seeded along defined outer surfaces of the endothelial stent 118 scaffold. This enables regionalized control of endothelial integration, potentially enhancing alignment with collector channels 302 or modulating local pore function.

Endothelial Seeding and Dual Layer Integration

Endothelial Cell Seeding & Integration

For optimal biological integration, the endothelial stent 118 is pre-seeded with a monolayer of Schlemm's canal 104 endothelial cells 1402 before implantation. Additional coatings, including extracellular matrix (ECM) proteins and nitric oxide-releasing compounds, may be applied individually or in combination to enhance adhesion, sustain viability, and mitigate fibrosis.

The seeded endothelial layer plays an important role in maintaining flow-regulated resistance, preventing excess drainage, and ensuring physiological intraocular pressure control.

TABLE 4

Comparative Summary Table

| Feature | Nitinol Stent (Permanent) | Bioabsorbable Stent (Temporary) | Hybrid Stent (Nitinol + Bioabsorbable) |
|---|---|---|---|
| Primary Benefit | Long-term Schlemm's canal support | Temporary endothelial regeneration | Combines mechanical support & biointegration |
| Durability | Permanent | Degrades over 1-6 months | Core remains, outer layer degrades |

TABLE 4-continued

| Comparative Summary Table | | | |
|---|---|---|---|
| Feature | Nitinol Stent (Permanent) | Bioabsorbable Stent (Temporary) | Hybrid Stent (Nitinol + Bioabsorbable) |
| Micropores | 0.5-2 μm | 0.5-2 μm | 0.5-2 μm |
| Coatings | ECM proteins, nitric oxide | VEGF, ECM, nitric oxide | VEGF, ECM, nitric oxide |
| Best for Patients with: | Severe glaucoma, Schlemm's canal collapse | Mild-to-moderate glaucoma, regenerable Schlemm's canal | Moderate-to-severe glaucoma, endothelial dysfunction |
| Less Ideal for: | Patients preferring biodegradable options | Advanced glaucoma needing long-term support | Highly fibrotic Schlemm's canal |

Schlemm's canal 104 plays a pivotal role in regulating intraocular pressure, with its inner wall 1514 endothelial cells 1402 (IWECs) forming transcellular pores and giant vacuoles 1518 to facilitate fluid movement, while its outer wall 1512 endothelial cells 1402 (OWECs) maintain a non-fenestrated barrier, directing aqueous fluid 204 into collector channels 302. Current glaucoma treatments, including trabecular bypass stents and microshunts, often bypass the natural outflow system rather than restoring its function, leading to complications such as fibrosis and foreign body responses.

The present inventions address these limitations by providing a bioengineered Schlemm's canal 104 endothelial stent 118 that is selectively endothelialized to replicate the canal's physiological function, thereby enhancing aqueous fluid 204 drainage while preserving the integrity of collector channels 302. By employing precise cell seeding techniques, microfluidic delivery methods, and pre-implantation bioreactor conditioning, these innovations offer a biomimetic, sustainable, and physiologically integrated solution to prevent disease progression and vision loss.

The process of harvesting, isolating, and selectively placing Schlemm's canal 104 cells onto a bioengineered endothelial stent 118 allows for refined and precise restoration of natural aqueous drainage. The following sequence describes the process of selective seeding of the bioengineered endothelial stent 118 by employing differential ECM coatings, microfluidic seeding, and mechanical stimulation.

Endothelial Cell Harvesting Process for Dual-Endothelization

Selectively endothelialized a Schlemm's canal 104 stent 118 restores natural aqueous fluid 204 outflow by replicating the endothelial architecture of Schlemm's canal 104. Successful dual-endothelialization enhances long-term intraocular pressure control and reduces dependence on pharmacologic treatments or additional surgical interventions.

Selective seeding of an endothelial stent 118 with inner wall 1514 endothelial cells 1402 (IWECs) on the inner portion of the external surface and outer wall 1512 endothelial cells 1402 (OWECs) on the outer surface ensures that specialized endothelial cells 1402 are positioned in their appropriate locations within Schlemm's canal 104. IWECs, seeded on the inner portion of the external surface of the endothelial stent 118 facing the trabecular meshwork 108, facilitate aqueous fluid 204 outflow through giant vacuole 1518 and transcellular pore formation. OWECs, seeded on the outer surface of the stent near the collector channels 302, provide a non-fenestrated endothelial barrier, directing aqueous fluid 204 into collector channels 302 while maintaining controlled fluid outflow.

TABLE 5

| How Different Flow Conditions Selectively Condition IWECs vs. OWECs | | | |
|---|---|---|---|
| Cell Type | Shear Stress Required | Response | Final Function |
| IWEC | 3.5-6.0 dynes/cm$^2$ | Develop pores and giant vacuoles | Facilitate aqueous fluid outflow |
| OWEC | 1.5-3.5 dynes/cm$^2$ | Form tight junctions and a non-fenestrated monolayer | Regulate fluid transition to collector channels |

Selective seeding may require biocompatible endothelial stent 118 materials that support cell adhesion and viability, such as collagen, hydrogels, or bioengineered polymers like PEG, PLGA, or PDMS. The endothelial stent 118 should also have porous or micropatterned surfaces to facilitate cell attachment and nutrient flow.

Layered Seeding and Extracellular Matrix (ECM) Coating

The inner portion of the external surface of the endothelial stent 118 (facing the trabecular meshwork 108) is coated with fibronectin and laminin, which promote IWEC adhesion, vacuole formation, and pore development. The outer surface of the endothelial stent 118 (facing the collector channels 302) is coated with collagen IV, which supports OWEC adhesion and the formation of a non-fenestrated monolayer. These coatings ensure that each endothelial cell 1402 type maintains its functional characteristics in the appropriate location.

Stepwise Cell Seeding Process

Stepwise seeding begins with the application of IWECs to the inner portion of the external surface of the endothelial stent 118, ensuring their placement facing the trabecular meshwork 108 rather than inside the stent lumen 506,704, 1004. IWECs may be pipetted onto the designated surface or infused via a syringe with a cannula to ensure targeted delivery. After allowing initial attachment, non-adherent cells are gently rinsed away to prevent random distribution.

Once IWECs are established, OWECs are seeded onto the outer surface of the endothelial stent 118, preferably near collector channels 302, where they function as a non-fenestrated barrier to direct aqueous fluid 204 into the outflow pathways. OWECs are applied using the same pipetting or infusion method, followed by a gentle rinse to remove any unbound cells.

Charge Modification and Hydrogel Encapsulation for Selective Cell Attachment

The endothelial stent 118 may incorporate charge-modified surfaces to enhance selective endothelial cell 1402 attachment. The inner portion of the external surface can be negatively charged to attract IWECs, while the outer surface can be neutral or slightly positively charged to promote OWEC adhesion.

Alternatively, a hydrogel encapsulation system can be applied to embed IWECs onto the inner portion of the external surface, while ensuring OWEC attachment on the outer surface. This method enhances cell retention and functionality before implantation.

In its intact state, the hydrogel encapsulation forms a thin transparent layer completely covering the endothelial stent 118. The hydrogel capsule is about 10 to 50 microns thick and degrades in about 5 to 14 days. As the hydrogel begins to dissolve small openings appear, revealing the microporous scaffold beneath. In its final stage the hydrogel capsule has fully degraded, leaving behind a functional endothelialized stent 118.

Stent Modification for Seeding of Mural Cells

Stents 1202 incorporating both endothelial cells 1402 and mural cells may require modifications to surface embodiments reserved for the stent 1202 that are limited to endothelial cells 1402. Modification of surface embodiments is needed to support the different adhesion properties, signaling requirements, and biomechanical roles of each cell type.

Mural cells do not migrate in the same manner as endothelial cells 1402 Mural cells tend to form clusters. Instead of following directional topographical cues provided by shallow microribs 1206 of 5 to 20 microns of height on the stent 1202 in some embodiments, mural cells may use an increased microribs 1206 height of 10-30 microns for anchoring mural cells. The spacing of microribs 1206 could be about 100-300 microns apart, which can facilitate the spread of mural cells and their interaction with endothelial layers.

Mural cells may also require nanotextured surfacing of the stent 1202 may consist of about 100-500 nm roughness. The nanotextured surface resembles a basement membrane that facilitates the adhesion and positioning of mural cells. The surface roughness may be between 500 nanometers to 2 microns to support mural cell attachment, and 1-5 microns in width for mural cell alignment and contractility.

An additional layer of Extracellular Matrix (ECM) is applied on the inner portion of the exterior surface of the stent 1202 facing the collector channels 302. An ECM that includes Collagen I, Elastin, and Perlecan, promotes adhesion and migration of mural cells. The surface of the stent 1202 can be modified so that the inner portion of the external surface is negatively charged (−10 to 20 mV) to favor endothelial cells 1402, and the outer portion positively charged (0 to +10 mV) to favor mural cells. The differential application of surface charging of the stent 1202 can enhance mural cell adhesion.

Application of Mural Cells

Mural cells and endothelial cells 1402 are not applied to the stent 1202 at the same time due to their different adhesion kinetics, proliferation rates, and functional roles. A staged process prevents mural cells from overpopulating the endothelial layer and ensures proper cell localization and optimized function. Instead, the process follows the sequence following endothelial seeding of Schlemm's canal 104 endothelial cells 1402 (SCEC) onto the inner surface of the stent 1202 facing the trabecular meshwork 108. In this stage, the endothelial cells 1402 attach to the extracellular matrix (ECM) with fibronectin and laminin to spread and form a monolayer. Certain biomaterials and coatings (e.g., hyaluronic acid, laminin, or VEGF-infused hydrogels) could promote mural cell adhesion to reinforce the endothelial layer Within about 48 hours following endothelial cell seeding, mural cells are introduced to the outside surface of the stent 1202 facing collector channels 302, where they interact with ECM proteins. The application of the optimal ratio of mural cells to endothelial cells 1402 is about 1 mural cell to every 3 to 7 endothelial cells 1402. An excessive density of mural cells could potentially impede pore formation and reduce aqueous fluid 204 outflow. Endothelial and mural cells are cultured together in a bioreactor under shear stress conditions to promote mutual signaling between them.

TABLE 6

Comparison of Flow Patterns in Bioreactors

| Flow Type | Shear Stress (dynes/cm$^2$) | Cell Alignment | Pore Formation | For Differentiating |
|---|---|---|---|---|
| Laminar Flow | 1.5-3.5 | Parallel to flow | Low | OWECs |
| Pulsatile Flow | 3.5-6.0 | Parallel with mechano-transduction | Moderate | IWECs |
| Oscillatory Flow | 4.0-7.5 | Bidirectional | High | Both IWECs and OWECs |

In an embodiment of the inventions, embedding endothelial cells 1402 and/or mural cells with or without seeding directly on the surface of the stent 1202 can enhance biocompatibility, functionality, and longevity of the stent 1202 with Schlemm's canal 104. Embedded cells can allow for faster cellular integration post-implantation. The presence of functional mural can also provide additional vascular stability and facilitate remodeling of Schlemm's canal 104. Endothelial-derived progenitor cells (EPCs) or stem cell-derived Schlemm's canal 104 endothelial cells embedded in the hydrogel can serve as a self-renewing population, capable of migrating outward and replacing senescent or damaged cells in Schlemm's canal 104.

The addition of mural cells to the endothelium results in a higher likelihood of increased stent 1202 longevity, consistent control of intraocular pressure, and reduction in stent 1202 failure over time.

TABLE 7

Inner vs. Outer Wall

| Location | Mural Cell Presence | Density | Function |
|---|---|---|---|
| Inner Wall | Sparse or absent | Low | Maximizes permeability for aqueous fluid drainage |
| Outer Wall | Present | Moderate to High | Regulates fluid resistance before aqueous fluid enters collector channels |

Incubation and Pre-Conditioning Before Implantation

After seeding, the endothelial stent 118 may be incubated for approximately five days, allowing sufficient time for cell attachment and early differentiation before implantation. During this period, the endothelial cells 1402 can be pre-conditioned in a bioreactor system, where exposure to simulated aqueous fluid 204 flow facilitates maturation and functional adaptation.

By ensuring precise endothelial cell 1402 placement, biocompatible material selection, and optimal pre-implantation conditioning, this approach enhances the effectiveness of Schlemm's canal 104 endothelial stent 118 in restoring physiological aqueous fluid 204 outflow and regulating intraocular pressure in glaucoma treatment.

TABLE 8

Estimated Time for Rinsing and Incubation Before Implantation

| Phase | Time Required | Key Process | Next Steps |
|---|---|---|---|
| Initial Adhesion | 0.5-2 hrs | OWECs begin attaching | Gentle rinse to remove non-adherent cells |
| Firm Adhesion | 4-6 hrs | Cells spread and strengthen attachment | Further incubation |
| Pre-Differentiation | 12-24 hrs | Tight junction formation begins | Stent can be implanted, or further matured |
| Full Maturation (Optional) | 48-72 hrs | Functional endothelial barrier forms | Enhances integration, improves implantation success |

Figure 12:
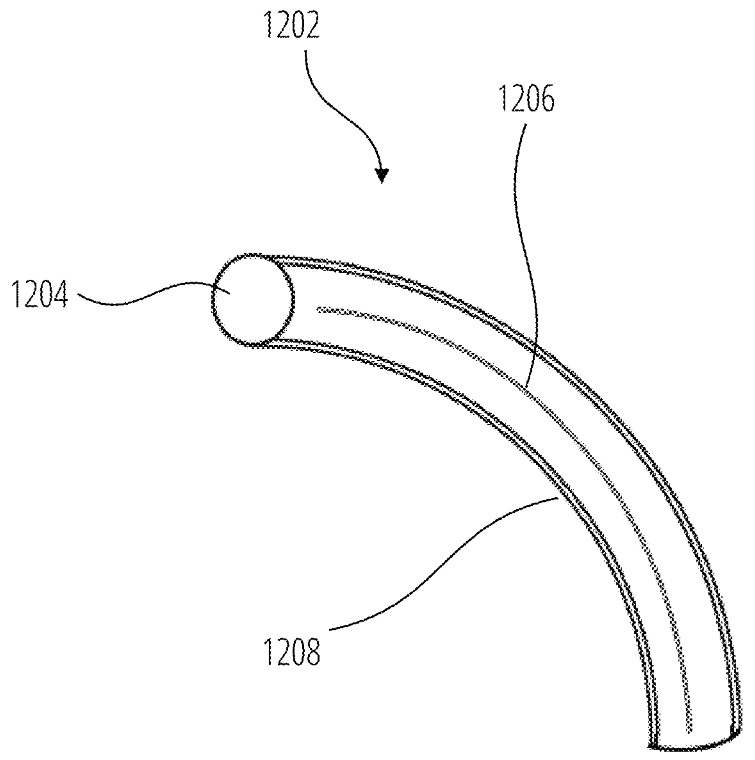
FIG. 12 is a line drawing of a sixth embodiment of the stent.

The stent 1202 of FIG. 12 could be made of the same materials listed above. In the FIG. 12 embodiment, the micropores 1106 are replaced by microrib 1206 structures that allow the aqueous fluid 204 to enter Schlemm's canal 104. The microrib 1206 structures could run the length of the stent 1202. In some embodiments, there is only one microrib 1206. In other embodiments, there are a plurality of microribs 1206. The stent 1202 may have a lumen 1204 to allow aqueous fluid 204 to enter the stent 1202 from the anterior chamber 110. In some embodiments, the stent 1202 has a hydrogel coating 1208.

Surface Microribs and Grooves for Endothelial Migration and Fluid Flow Optimization In addition to microtexturing, nanoporous structures, and wettability modifications, the incorporation of longitudinal grooves and/or longitudinal microribs 1206 on the exterior surface of the endothelial stent 118 provides topographical guidance for endothelial cell 1402 migration and enhances aqueous fluid 204 outflow dynamics. These microgrooves and microrib 1206 act as cellular migration pathways, directing endothelial expansion from the endothelial stent 118 onto the Schlemm's canal 104 wall, thereby promoting seamless integration with native endothelium, while also allowing for proper aqueous fluid 204 flow dynamics. One possible set of dimensions is included in Table 9.

TABLE 9

Range of Microgroove Dimensions

| Feature | Preferred Range | Purpose |
|---|---|---|
| Groove Depth | 5-20 μm | Provides topographical guidance for endothelial migration and prevents excessive cell adhesion in valleys. |
| Groove Width | 50-200 μm | Balances fluid permeability and cellular migration along the grooves. |
| Groove Spacing | 50-200 μm | Ensures endothelial cells can span adjacent grooves while maintaining uniform coverage. |
| Sidewall Angle | 60-90° | Enhances shear stress response and prevents excessive cellular accumulation at the base of grooves. |
| Surface Roughness (inside grooves) | 100-500 nm (nanotextured) | Enhances mechanosensitive responses of endothelial cells, mimicking native Schlemm's canal architecture. |
| Groove Orientation | Longitudinal (parallel to aqueous humor flow) | Aligns cells with physiological Schlemm's canal architecture, optimizing migration and outflow regulation. |

The microribs 1206 are longitudinally aligned to match the curvature of Schlemm's canal 104, ensuring consistent cellular guidance and controlled aqueous fluid 204 transport. The microribs 1206 may have a height between approximately 5 and 20 μm, with spacing in the range of about 50 to 200 μm to support cell adhesion and inter-rib migration while maintaining an unobstructed fluid pathway. The number of microribs 1206 may vary based on the stent 1202 diameter and material flexibility, typically ranging between 6 and 20 microribs 1206 around the circumference.

To further optimize function, the microribs 1206 may include nanoporous surface features with pore sizes ranging from approximately 100 to 500 nanometers. These nanopores enhance endothelial mechanosensitivity and responsiveness to shear stress. Such structural modifications may be introduced using fabrication techniques including laser microtexturing, soft lithography, or direct micromolding, selected based on the material composition of the stent 1202. The stent 1202 material may comprise nitinol, bioabsorbable polymers such as PLGA, or hybrid composites that combine a metallic core with a biodegradable outer cladding. In particular, titanium-based surfaces—including those found in nitinol stents—can be modified using established surface treatment methods to improve endothelial cell 1402 adhesion and biointegration.

These surface modifications collectively promote rapid endothelialization, improved adhesion strength, and sustained mechanotransduction, ensuring that endothelial cells 1402 remain functionally active within the stent 1202 over extended periods. These modifications can be tailored to promote endothelial cell 1402 attachment and proliferation, which is important for achieving rapid re-endothelialization of the Schlemm's canal 104 wall and improving aqueous fluid 204 outflow.

By mimicking native Schlemm's canal 104 endothelium, these structural enhancements optimize aqueous fluid 204 outflow regulation, improving intraocular pressure control in glaucoma patients while ensuring long-term biocompatibility and stent 1202 performance.

Table 11 provides representative dimensions and orientations for microrib 1206 structures that may be incorporated into the stent 1202 design. However, variations beyond these values may also be implemented, and the inventions are not limited to the specific ranges listed. Tables 10 and 11 provide further details regarding the microrib 1206 design.

TABLE 10

Examples of Dimensional Tolerances of the Endothelial-Seeded Stent

| Feature | Dimension (Preferred Embodiment) | Tolerance (±μm) | Notes |
|---|---|---|---|
| Outer Diameter | 250-350 μm | ±10 μm | Matches Schlemm's canal diameter |
| Lumen Diameter | 100-200 μm | ±5 μm | Allows controlled aqueous flow |
| Wall Thickness | 50-75 μm | ±5 μm | Balances strength with flexibility |
| Pore Diameter | 1.0-3.0 μm | ±0.5 μm | Mimics natural Schlemm's canal pores |
| Pore Density | 300-1,000 pores/mm$^2$ | ±50 pores/mm$^2$ | Optimized for permeability |
| Stent Length | 6.0-8.0 mm | ±50 μm | Covers a functional segment of Schlemm's canal |
| Radius of Curvature | ~7.5 mm | ±0.5 mm | Matches limbal curvature |

TABLE 11

Expansion & Mechanical Properties of Endothelial-Seeded Stent

| Feature | Specification | **Tolerance (±%) | Notes |
|---|---|---|---|
| Radial Expansion (Nitinol Stent) | 5-15% | ±2% | Ensures anchoring within Schlemm's canal |
| Degradation Time (Bioabsorbable Stent) | 3-12 months | ±1 month | Allows endothelial remodeling |
| Elastic Modulus (Compliance) | 50-150 kPa | ±10 kPa | Ensures flexibility in Schlemm's canal |
| Shear Stress Resistance | 1-6 dynes/cm$^2$ | ±0.5 dynes/cm$^2$ | Maintains endothelial adhesion |

TABLE 12

Microrib Design Examples

| Microrib Feature | Example Range | Intended Function |
|---|---|---|
| Rib Height | ~5-20 μm | Provides structural guidance for endothelial migration without impeding fluid flow |
| Rib Spacing | ~50-200 μm | Balances endothelial migration support with aqueous humor drainage |
| Orientation | Longitudinal | Aligns endothelial cells and fluid flow with Schlemm's canal curvature |
| Number of Ribs | ~6-20 | Optimized based on stent diameter and material properties |
| Nanopore Diameter (optional) | ~100-500 nm | Enhances endothelial mechanotransduction and nutrient exchange |
| Fabrication Methods | Laser microtexturing, soft lithography, micromolding | Adaptable for different stent materials (Nitinol, PLGA, hybrid) |

Figure 13:
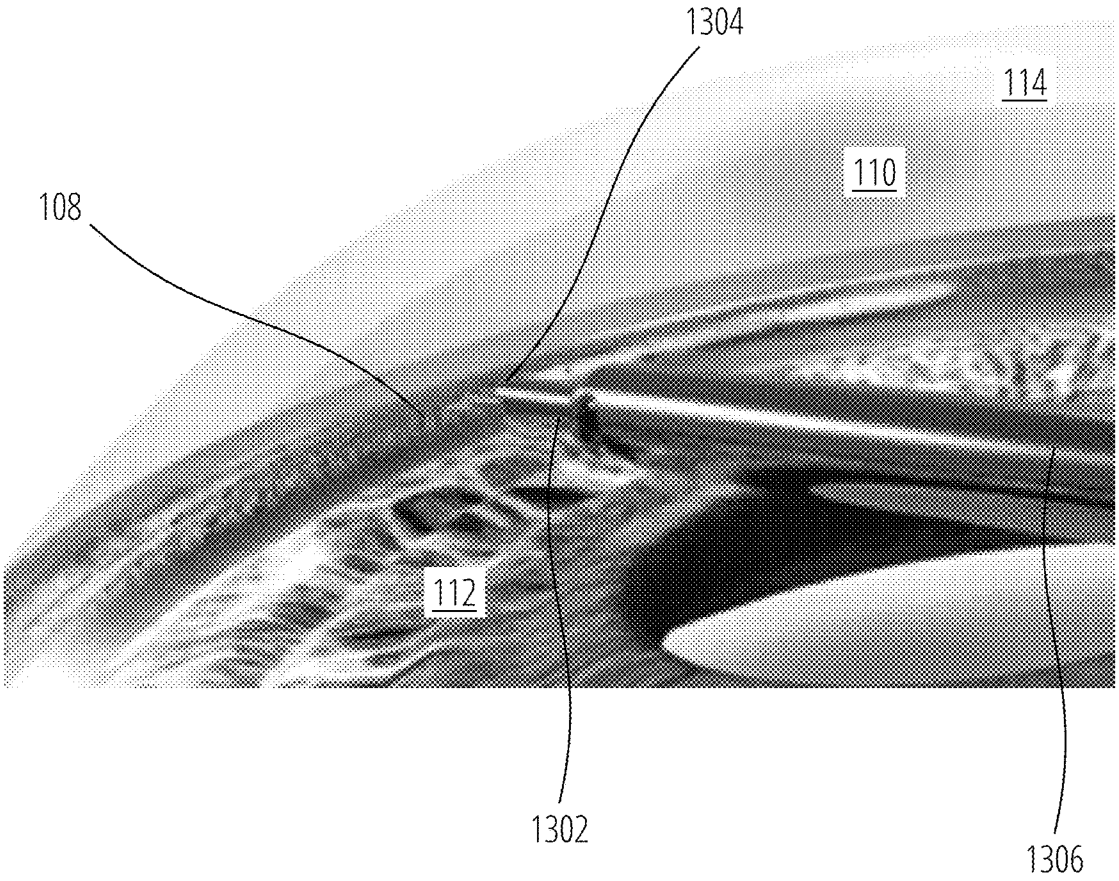
FIG. 13 illustrates the insertion of a stent into the eye according to one embodiment.
Figure 14A:
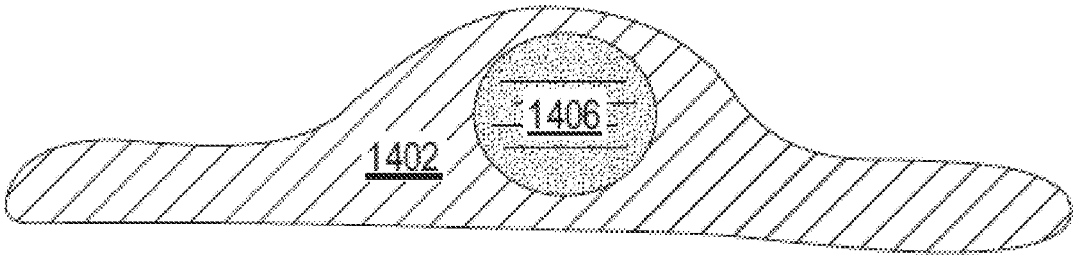
FIG. 14A-D shows the sequence of the formation of a giant vacuole.
Figure 14B:
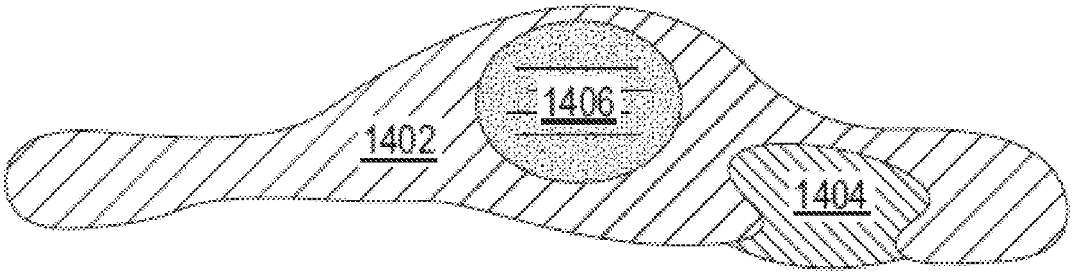
Figure 14C:
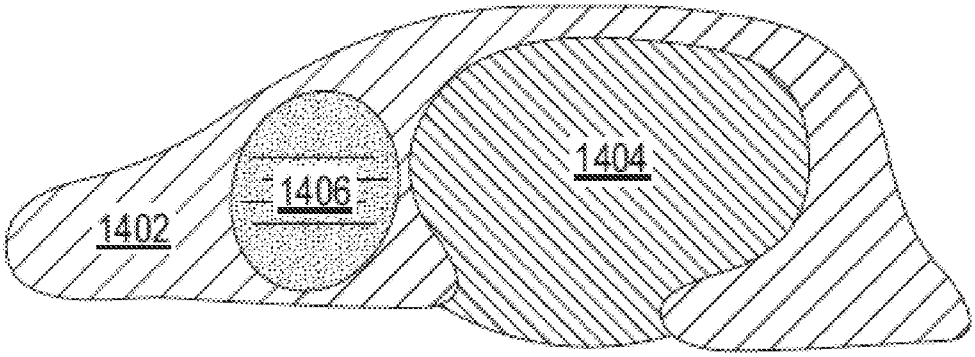
Figure 14D:
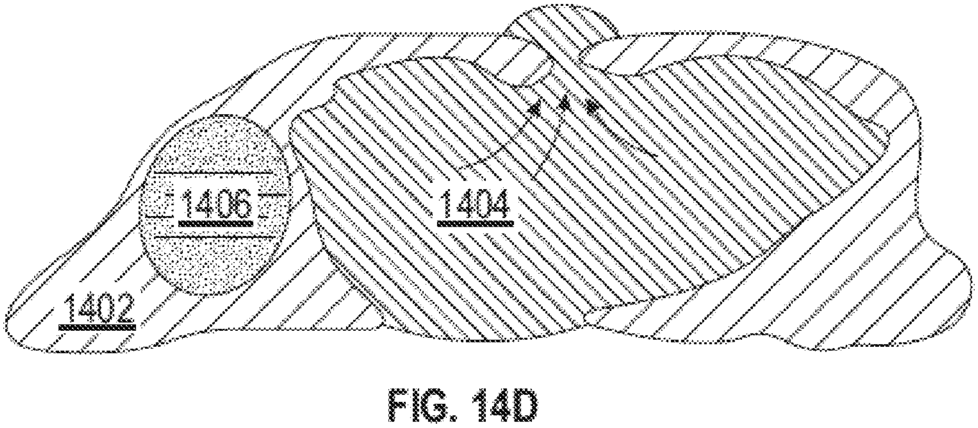

FIG. 13 is an animation of an endothelial stent 118 being inserted through the trabecular meshwork 108 and into Schlemm's canal 104. An incision could be made in the clear cornea 114 on the opposite side of the eye 102. A catheter of a syringe-like introducer 1302 with a pusher may insert the endothelial stent 118 through an incision 1304 in the trabecular meshwork 108.

The introducer is 1306. The trochar is 1302 and may have a sharp tip for creating an incision in the trabecular meshwork 108. The introducer 1306 may have a barrel that may accommodate one or more stents. In some embodiments, a trochar 1306 is used to assist in the guidance of the introducer 1302. Some types of trochars 1306 have a sharp point at the front of the introducer 1302 to make an incision 1304 into the trabecular meshwork 108. The introducer 1302 may have a sharp trochar 1306 at the front of the introducer 1302, thus eliminating the need for a blade instrument. The introducer 1302 may require a barrel that is sized to fit two endothelial stents 118 in consecutive fashion. For example, a patient may benefit by having two endothelial stents 118 placed in Schlemm's canal 104 at different locations.

Post-Seeding Maturation & Implantation

After selective cell placement, the endothelial stent 118 may undergo maturation in a bioreactor where:

- Flow conditions simulate Schlemm's canal 104 physiology, reinforcing IWEC and OWEC differentiation.
- Cell attachment and function are verified using microscopy and functional assays.
- The endothelial stent 118 is then surgically implanted into Schlemm's canal 104, where it integrates with native tissue and restores physiological aqueous fluid 204 outflow.

Delivery & Insertion Mechanisms

The endothelial-seeded stent 118 is designed for minimally invasive implantation using an introducer-based delivery system consisting of a flexible microcatheter or hollow metallic cannula. An endothelial stent 118 prepared with endothelial cells 1402 is inserted into the proximal end of the introducer 1302 that has a lumen and a pusher rod mechanism at the distal end of the introducer 1302. The lumen of the introducer 1302 can be configured to hold a plurality of endothelial stents 118 for application at selected locations within Schlemm's canal 104. The introducer 1302 is inserted through a corneal incision to access Schlemm's canal 104. In some instances, the introducer 1302 and/or the pusher rod may be flexible and have a small enough diameter to extend at least partially circumferentially within the canal 104. In certain variations, a positioning device may be used to assist placement and alignment. The positioning device may include a trochar 1306, a second rod, a gripper, a hook, a clamp, or similar mechanisms designed to stabilize or guide the stent during implantation. See FIG. 16, block 1612, and FIG. 13. In certain embodiments, the introducer 1302 may be introduced into Schlemm's canal 104 through a scleral incision (ab externo approach) rather than through a corneal incision (ab interno approach). A scleral entry site provides direct access to the canal and may be advantageous in cases where visualization or canaloplasty techniques are employed. This document therefore contemplates both ab interno and ab externo routes of access, including corneal, scleral, or other incisions that provide access to Schlemm's canal.

In some variations, the methods include a diagnostic device comprising a light source, ultrasound, or optical coherence tomography to assess the position of the endothelial stent 118 and the location of collector channels 302. For example, the introducer 1302 may include imaging guidance or positioning features to ensure proper alignment with the collector channels 302. However, the endothelial stent 118 is not dependent on a specific delivery method, and variations in introducer 1302 design may be used.

The introducer 1302 and/or endothelial stent 118 can be preloaded with a high viscosity fluid, such as sodium hyaluronate, to lubricate surfaces to reduce loss of endothelial cells 1402 on the endothelial stent 118 during stent delivery, or dilating Schlemm's canal 104 to facilitate stent insertion. These features may be incorporated to optimize endothelial stent 118 protection and positioning, but are not required for successful implantation.

The leading tip of the introducer 1302 can be beveled to create an angled incision for entry into the trabecular meshwork 108 extending into Schlemm's canal 104. A pushing rod within the lumen of catheter is activated by the surgeon to propel the endothelial stent 118 through the lumen of the introducer 1302 and into Schlemm's canal 104.

Real-time optical coherence tomography (OCT), aqueous humor angiography, or similar in vivo visualization techniques may be used to locate, guide, and assess the placement of the endothelial-seeded stent 118 within Schlemm's canal 104. OCT imaging allows for precise visualization of the endothelial stent 118 relative to the canal walls, ensuring optimal positioning against the inner wall 1514 of Schlemm's canal 104, where endothelial integration and physiological aqueous fluid 204 outflow occur. By identifying the collector channel 302 ostia, OCT guidance enables targeted positioning of the endothelial stent 118 in regions of maximal outflow potential, enhancing drainage efficiency. See FIG. 16, block 1614, and block 1616.

Methods for OCTA Imaging of Aqueous Flow

Additionally, OCT imaging provides a non-invasive means of monitoring post-implantation endothelial stent 118 behavior, detecting malpositioning, endothelial cell 1402 coverage, structural integrity, or potential complications such as fibrosis or tissue disruption. Early detection of these issues allows for timely intervention, including repositioning or adjunctive therapy. See block 1618.

Aqueous humor angiography complements OCT by assessing the functional efficacy of the endothelial stent 118 in real-time. This technique visualizes aqueous fluid 204 outflow pathways and flow patterns, confirming that the endothelial stent 118 successfully restores physiological drainage through Schlemm's canal 104 and collector channels 302. By identifying areas of segmental flow restriction or non-perfusion, aqueous angiography enables objective verification of stent performance and endothelial function, ensuring long-term therapeutic benefit.

OCT and OCTA imaging may be employed to evaluate shear stress distribution and segmental flow dynamics along Schlemm's canal. OCT provides high-resolution structural assessment of canal lumen geometry and wall compliance, while OCTA enables visualization of circumferential and collector channel flow patterns. These modalities can be applied in a 360° analysis of Schlemm's canal using sequential limbal scans, swept-source OCT (SS-OCT), and image reconstruction techniques. The high scanning speed of SS-OCT permits near-continuous data acquisition along the limbal circumference, which can then be processed with automated reconstruction software to generate three-dimensional maps of Schlemm's canal, including lumen size, wall thickness, and focal areas of collapse. In addition, serial radial scans around the limbus can be digitally stitched to form a circumferential model of Schlemm's canal, analogous to OCT cube reconstructions of the retina.

OCT and OCTA for Assessing Schlemm's Canal Endothelial Cell Function

In certain embodiments, optical coherence tomography (OCT) and optical coherence tomography angiography (OCTA) are employed to assess the functionality of Schlemm's canal endothelial cells in vivo. These modalities, particularly when integrated with AI-based analytics, provide structural and functional biomarkers of endothelial health that correlate with pore formation, vacuole development, shear responsiveness, and aqueous outflow capacity.

OCT Structural Assessment. OCT enables micron-scale visualization of Schlemm's canal 104 and adjacent trabecular meshwork 108. Cross-sectional imaging can evaluate canal lumen geometry, wall compliance, and focal areas of separation between the endothelium and juxtacanalicular tissue. Transient IOP perturbations, induced by suction or air-puff stimuli, allow OCT to record real-time canal lumen deformation. Reduced compliance or persistent wall separation indicates endothelial dysfunction or dropout.

OCTA Functional Assessment. OCTA measures fluid scatter within Schlemm's canal 1041, providing flow-based indicators of endothelial activity. Segmental flow mapping identifies regions of reduced signal intensity corresponding to dysfunctional endothelial zones. By combining OCTA with physiologic maneuvers such as transient IOP modulation or episcleral venous pressure changes, the responsiveness of endothelial cells to shear stress can be determined. A blunted OCTA response suggests impaired pore formation or reduced shear sensitivity.

Combined OCT/OCTA with AI Analytics. Integrating OCT structural features with OCTA flow signals enables the generation of composite maps of Schlemm's canal endothelial function. AI-based analysis can highlight regions of low wall compliance and diminished flow signals consistent with stiffened endothelium, as well as structural-flow mismatches suggestive of endothelial dysfunction rather than mechanical obstruction, and dynamic changes in pore function and nitric oxide-mediated relaxation over time.

Clinical Utility. These imaging methodologies permit precise identification of dysfunctional canal segments that may benefit from selective endothelial cell removal or stent-based re-endothelialization. By providing non-invasive, real-time biomarkers of Schlemm's canal endothelial health, OCT and OCTA serve both diagnostic and therapeutic guidance functions.

In some embodiments, ultrasound imaging is also contemplated as a diagnostic modality, where acoustic backscatter and Doppler ultrasound parameters are employed to infer localized shear stress and fluid-wall interactions within Schlemm's canal 104. These diagnostic approaches may be used independently or in combination to guide implantation, assess endothelial stent 118 function, and optimize patient-specific therapy.

In one aspect, a bioengineered endothelial-seeded stent 118 for Schlemm's canal 104 includes a biocompatible or biodegradable scaffold, a stent-seeding system promoting endothelial adhesion and functional integration, and micropores configured for pressure-responsive aqueous humor drainage. The bioengineered endothelial-seeded stent 118 may also include a nitinol frame with a self-expanding structure combined with a biodegradable polymer such as poly(lactic-co-glycolic acid) (PLGA), polyethylene glycol (PEG), or polydimethylsiloxane (PDMS) with a controlled degradation profile. In certain embodiments, the scaffold incorporates both a permanent and a bioabsorbable layer. The endothelial stent 118 may further comprise a titanium oxide coating, a nitric oxide-releasing polymer, and an extracellular matrix (ECM) protein layer such as fibronectin, laminin, or collagen IV to enhance endothelialization and reduce inflammatory response. The walls of the bioengineered endothelial-seeded stent 118 may include a microporous structure, where the micropores range from approximately 0.5-2 μm to replicate endothelial permeability, and may be distributed uniformly or asymmetrically to direct aqueous outflow.

TABLE 13

Structural and Functional Defects of Schlemm's Canal

| Defect | Imaging Signature (OCT/ OCTA/Ultrasound) | Functional Impact | Therapeutic Options |
|---|---|---|---|
| Segmental Constriction | Localized lumen narrowing on OCT; reduced circumferential OCTA flow; elevated shear stress on Doppler ultrasound | Focal resistance, impaired circumferential outflow | Targeted stent placement, canaloplasty dilation, endothelial reseeding |
| Kinking/ Tortuosity | Bending or angular distortion of canal lumen on OCT; irregular contour in reconstructed maps | Interrupts laminar flow, creates turbulence, endothelial stress | Stent realignment, scaffold reinforcement, hydrogel sleeve placement |
| Focal Collapse | Inward buckling or wall apposition on OCT; absent OCTA signal; ultrasound shows reduced wall compliance | Lumen closure, impaired pore function, segmental flow arrest | Stent expansion, canaloplasty balloon dilation, endothelial replacement |
| Obstructive Tissue Bridges | Hyper-reflective bands spanning lumen on OCT; focal OCTA voids; acoustic backscatter irregularities on ultrasound | Partial occlusion of outflow, asymmetric segmental drainage | Mechanical or enzymatic removal, microcatheter clearing, stent-assisted repair |
| Segmental Dysfunction Without Obstruction | Intact lumen on OCT; diminished OCTA flow response; shear-insensitive profile on Doppler ultrasound | Endothelial dysfunction despite preserved canal structure | Selective endothelial removal, reseeding with bioengineered or autologous cells |

In certain embodiments, this document contemplates classification of structural and functional defects within Schlemm's canal 104 that contribute to impaired aqueous humor outflow. These defects may occur focally or segmentally and are amenable to detection by OCT, OCTA, or ultrasound imaging. Defining these defects allows for targeted therapy, including selective cell removal, stent implantation, or canaloplasty, directed specifically to dysfunctional canal segments.

Segmental constriction represents localized narrowing of Schlemm's canal 104*al*, often due to endothelial cell loss or fibrosis, and is associated with reduced outflow and elevated shear stress. Kinking or tortuosity occurs when the canal lumen is mechanically deformed, interrupting laminar flow and creating turbulent stresses on endothelial cells. Focal collapse involves inward buckling of the canal wall, producing lumen closure and loss of pore-mediated outflow. Obstructive tissue bridges, such as fibrotic bands or endothelial overgrowth, traverse the lumen and partially occlude outflow pathways. Finally, segmental dysfunction without obstruction describes regions where the canal remains structurally intact but endothelial cells exhibit impaired shear responsiveness or pore formation, resulting in flow deficits detectable by OCTA.

By categorizing these defects and correlating them with imaging readouts, clinicians and surgeons can tailor interventions to specific canal pathologies. The therapeutic strategies may include selective removal of dysfunctional cells, mechanical or enzymatic clearing of obstructive tissue, canaloplasty-based dilation, or implantation of endothelial stents 118. Integration of OCT, OCTA, and ultrasound imaging enables real-time identification and monitoring of these defects, ensuring precise and patient-specific treatment of Schlemm's canal dysfunction.

FIG. 14A-D is an animation of different morphologies in the growth of a giant vacuole 1404 within an endothelial cell 1402 of Schlemm's canal 104. They can form outpuchings into the anterior chamber which appear as "signet rings." The giant vacuole 1404 is filled with aqueous fluid 204 that is released into the lumen of Schlemm's Schlemm's canal 104. Giant vacuoles 1404 form when aqueous fluid 204 from the anterior chamber 110 pushes against the basal side of endothelial cells 1402. Giant vacuoles 1404 are thought to be involved in regulating intraocular pressure. The giant vacuoles 1404 are pressure- and time-dependent structures. The size and density of giant vacuoles 1404 increase with intraocular pressure. Giant vacuoles 1404 disappear within minutes after intraocular pressure is lowered. FIG. 14A-D shows the evolution of an endothelial cell 1402 giant vacuole 1404. The dark round area inside the endothelial cell 1402 is the nucleus 1406 of the endothelial cell 1402.

Figure 15A:
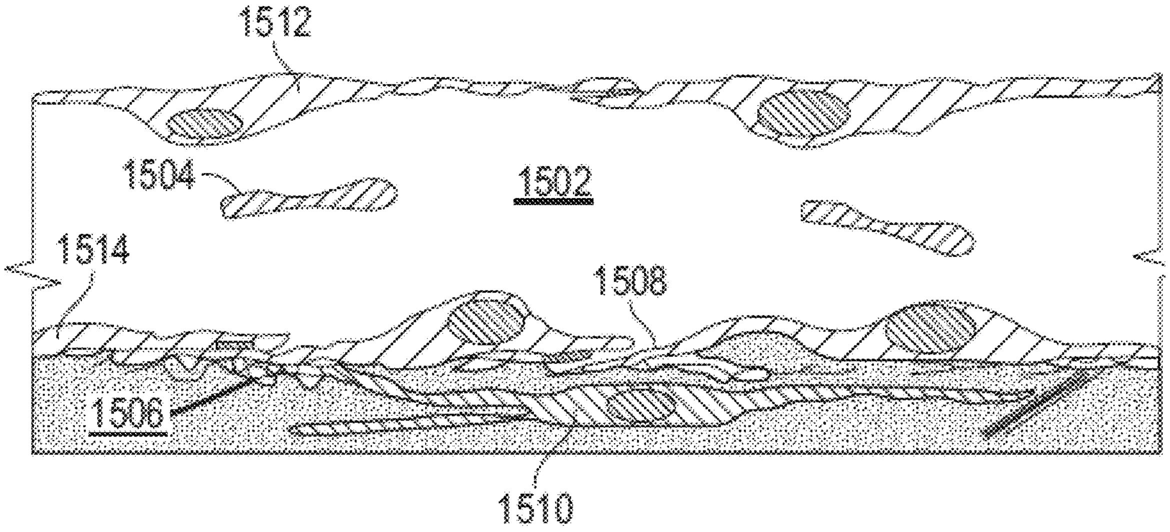
FIG. 15A illustrates the cellular structure of Schlemm's canal and the surrounding area during normal operation.
Figure 15B:
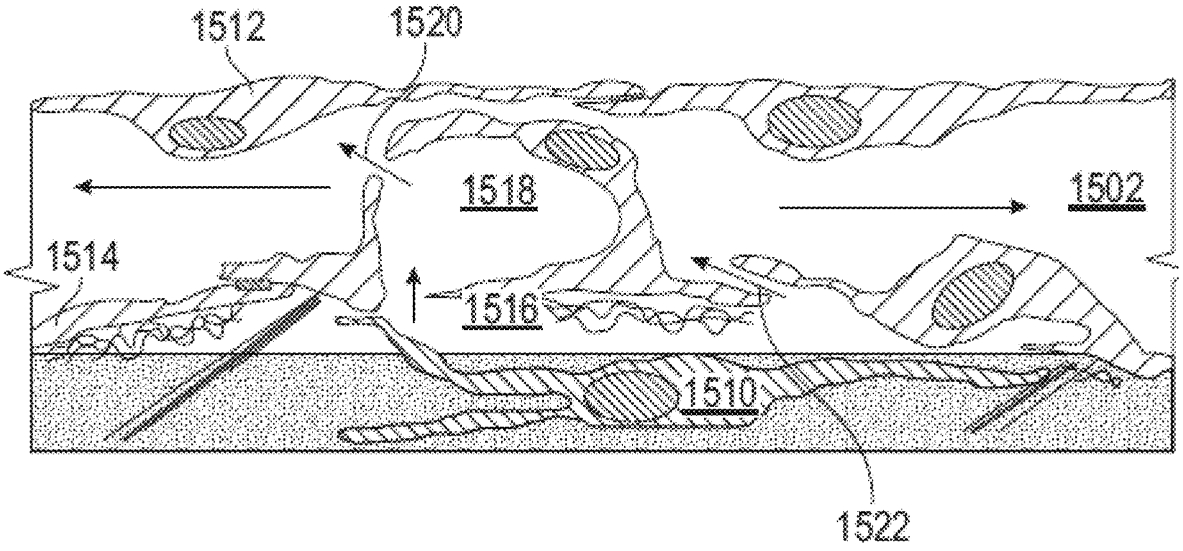
FIG. 15B illustrates the cellular structure of Schlemm's canal and the surrounding area with an elevated ocular pressure.

FIG. 15A-B shows the functionality of Schlemm's canal 104 at a cellular level. The Schlemm's canal lumen 1502 is bounded by the outer wall 1512 and the inner wall 1514. Below the inner wall 1514 are the trabecular meshwork cells 1510. The juxtatrabecular meshwork tissue 1506 is located adjacent to the anterior wall of Schlemm's canal. FIG. 15A shows normal operation and FIG. 15B shows Schlemm's canal 104 with an elevated ocular pressure.

Some of the key types of cells and structures associated with Schlemm's canal 104 that are related to the endothelial stent 118. The endothelial stent 118 is delivered to Schlemm's canal lumen 1502 during the procedure in FIG. 13. The intercellular tight junction 1508 permits aqueous fluid 204 to move from the trabecular meshwork 108 into the Schlemm's canal 104 between the trabecular meshwork cells 1510 of the inner wall 1514. Tight junctions are intercellular adhesion complexes in epithelia and endothelia that control paracellular permeability.

In FIG. 15B, the discontinuous basement membrane 1516 allows aqueous fluid 204 to enter an endothelial cell 1402. A large opening (giant vacuole 1518) in the endothelial cell 1402 filled with aqueous fluid 204 that will be released into Schlemm's canal 104. The aqueous fluid 204 will flow through intracellular pore 1520 in an endothelial cell 1402 that releases aqueous fluid 204 into Schlemm's canal 104. The aqueous fluid 204 may also flow through paracellular pore 1522 into Schlemm's canal 104. The paracellular flow serves to slow the aqueous fluid 204 flow into Schlemm's canal 104.

In block 1612, routine 1600 inserts the endothelial-seeded stent 118 into Schlemm's canal 104 via a microcannula or introducer 1006, 1302. In block 1614, routine 1600 utilizing real-time optical coherence tomography (OCT) imaging to visualize the placement relative to canal walls and adjacent collector channel 302 openings. In block 1616, routine 1600 adjusts a position to optimize opposition against an inner wall of Schlemm's canal 104. In block 1618, routine 1600 confirms aqueous humor outflow restoration via aqueous angiography by assessing fluid dynamics through the endothelial-seeded stent 118 and the adjacent collector channel 302 openings.

Figure 17:
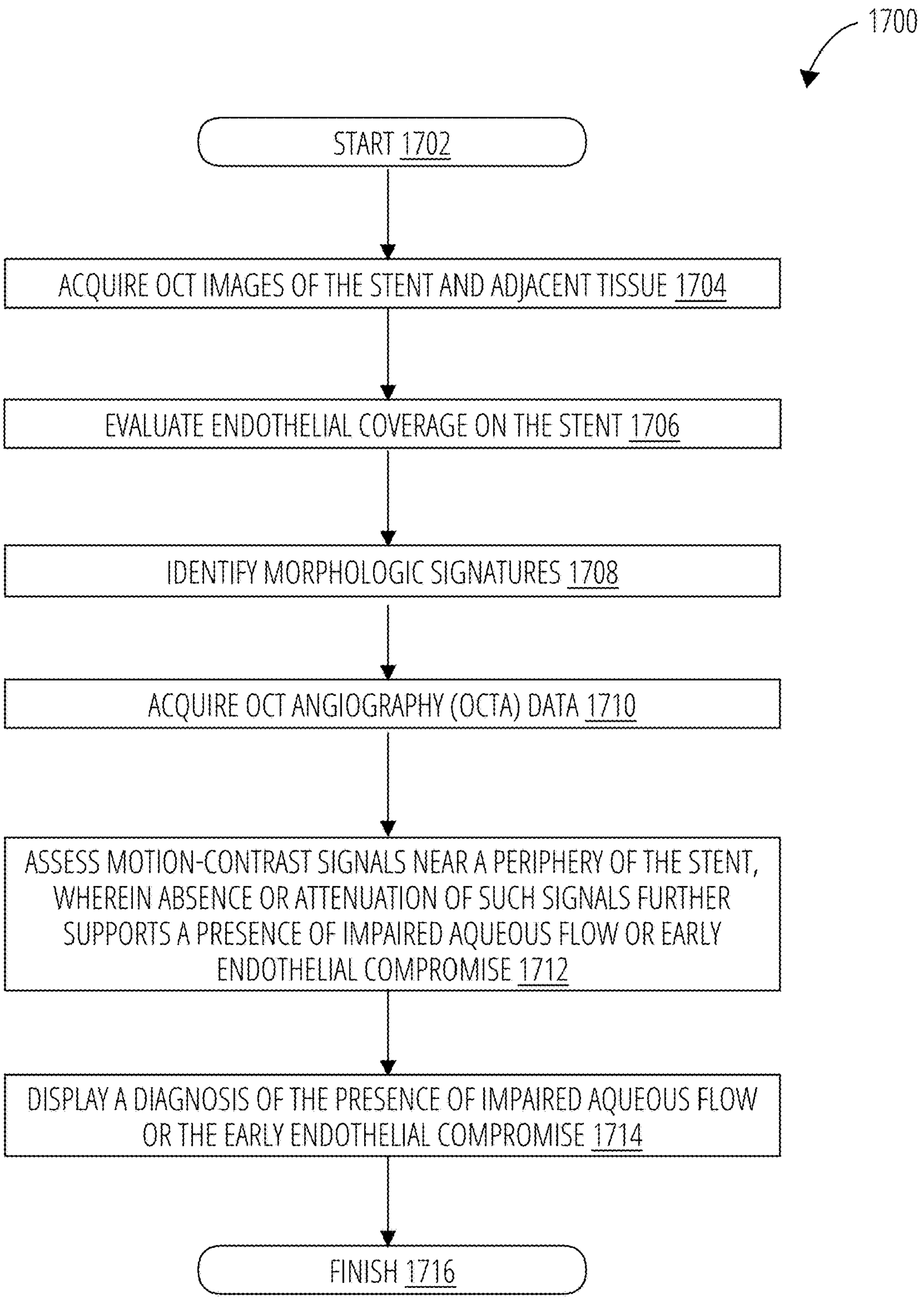
FIG. 17 illustrates a routine 1700 for detecting subclinical endothelial dysfunction in a stent-implanted Schlemm's canal.

FIG. 17 shows one possible method for evaluating the effectivity and diagnosing problems with the endothelial stent 118 as installed in the eye 102. The steps in FIG. 17 are optional, and can be eliminated without departing for the scope of this document. In block 1704, routine 1700 acquires OCT images of the endothelial stent 118 and/or the adjacent tissue. In some embodiments, the OCT images are used to evaluate the endothelial cell coverate on the embedded endothelial stent 118. See block 1706. In block 1708, routine 1700 identifies morphologic signatures suggestive of reduced endothelial integration or early fibrosis, including surface irregularity, thinning, or hyperreflective deposits near an interface between a stent and tissue. In block 1710, routine 1700 acquires OCT angiography (OCTA) data. In block 1712, routine 1700 assesses motion-contrast signals near the periphery of the stent, wherein the absence or attenuation of such signals further supports the presence of impaired aqueous flow or early endothelial compromise. In block 1714, routine 1700 displays a diagnosis of the presence of impaired aqueous flow or the early endothelial compromise.

Post-Implantation Imaging and Verification

In certain embodiments, structural optical coherence tomography (OCT) and OCT angiography (OCTA) are employed intraoperatively or postoperatively to monitor endothelial integration and functional behavior of the endothelial stent 118 within Schlemm's canal 104. These modalities are not used for navigation or guidance, but rather to assess morphological and dynamic cellular responses associated with the stent-tissue interface.

OCT enables high-resolution visualization of the stent's position relative to the canal walls and surrounding tissue, allowing longitudinal evaluation of endothelial cell coverage, multilayer cell configurations, and the formation of endothelial microstructures such as vacuoles and pores. Postoperative OCT may reveal the development of endothelial cell domes, bridging patterns, or cell-layer thickening, which may correlate with physiological regulation of aqueous humor resistance.

OCTA, in turn, permits non-invasive visualization of dynamic flow within Schlemm's canal 104 and collector channels 302*s*, highlighting endothelial-mediated flow modulation. This includes identifying segmental flow patterns, pulsatility of aqueous humor, and variations in shear stress responsiveness across the stent-endothelium complex. OCTA imaging may also reveal flow deviations attributable to endothelial cell 1402 remodeling or microobstruction, providing insight into long-term stent efficacy.

Unlike existing devices, which are monitored by OCT or OCTA without regard to endothelial cell 1402 morphology or function, the present invention integrates cellular behavior analysis and dynamic modulation via seeded endothelial constructs. Several glaucoma stents have incorporated optical coherence tomography (OCT) to assist in device placement or surgical navigation (e.g., U.S. Pat. No. 10,993,840, US20250072837). While such systems enable visualization of Schlemm's canal 104 during implantation, they do not provide insight into postoperative endothelial behavior, cellular integration, or fluid dynamics associated with transplanted endothelial cells 1402. The disclosed invention addresses this gap by employing OCT and optionally OCT angiography (OCTA) for real-time, postoperative monitoring of endothelial configurations, including vacuole formation, pore density, and flow-modulated integration patterns.

Selective Seeding of Endothelial Cells from Schlemm's Canal

A selectively endothelialized Schlemm's canal 104 stent 118 restores natural aqueous fluid 204 outflow by replicating the endothelial architecture of Schlemm's canal 104. Successful dual-endothelialization enhances long-term intraocular pressure control and reduces dependence on pharmacologic treatments or additional surgical interventions.

Selective seeding of an endothelial stent 118 with inner wall 1514 endothelial cells 1402 (IWECs) on the inner portion of the external surface and outer wall 1512 endothelial cells 1402 (OWECs) on the outer surface ensures that specialized endothelial cells 1402 are positioned in their appropriate locations within Schlemm's canal 104. IWECs, seeded on the inner portion of the external surface of the endothelial stent 118 facing the trabecular meshwork 108, facilitate aqueous fluid 204 outflow through giant vacuole 1518 and transcellular pore formation. OWECs, seeded on the outer surface of the endothelial stent 118 near the collector channels 302, provide a non-fenestrated endothelial barrier, directing aqueous fluid 204 into the collector channels 302 while maintaining controlled fluid outflow.

Selective seeding may require biocompatible endothelial stent 118 materials that support cell adhesion and viability, such as collagen, hydrogels, or bioengineered polymers like PEG, PLGA, or PDMS. The endothelial stent 118 should also have porous or micropatterned surfaces to facilitate cell attachment and nutrient flow.

Layered Seeding and Extracellular Matrix (ECM) Coating

The inner portion of the external surface of the endothelial stent 118 (facing the trabecular meshwork 108) may be coated with fibronectin and laminin, which promote IWEC adhesion, vacuole formation, and pore development. The outer surface of the endothelial stent 118 (facing the collector channels 302) may be coated with collagen IV, which supports OWEC adhesion and the formation of a non-fenestrated monolayer. These coatings ensure that each endothelial cell 1402 type maintains its functional characteristics in the appropriate location.

TABLE 14

Stent Surface Layout for Dual ECM Coating

| Stent Surface Region | Cell Type Supported | ECM Coating | Function |
|---|---|---|---|
| Inner Portion of the External Surface | Schlemm's canal endothelial cells | Fibronectin, Lamminin, Collagen IV, Heparan Sulfate Proteoglycans | Supports permeability, pore formation, and vacuole development |
| Outer Portions | Mural cells (pericytes, smooth muscle-like cells | Collagen I & III, Elastin, Hyaluronic Acid, VEGF | Enhances mural cell attachment, regulates outflow resistance. |

TABLE 15

| | Thickness of Each Coating Bioabsorbable Layer | | | |
|---|---|---|---|---|
| Coating Type | Location on Stent | Function | Thickness Range | Drying Time Before Next Layer |
| Extracellular Matrix (ECM) Coating for IWECs | Inner portion of external stent's surface | Promotes IWEC adhesion, vacuole formation, and transcellular pore development | 5-50 μm | 4-12 hours at 37 °C in a humidity-controlled chamber |
| Extracellular Matrix (ECM) Coating for OWECs | Outer surface | Supports OWECs and forms non-fenestrated barrier near collector channels 302 | 5-50 μm | 4-12 hours |

TABLE 15-continued

| Thickness of Each Coating Bioabsorbable Layer | | | | |
|---|---|---|---|---|
| Coating Type | Location on Stent | Function | Thickness Range | Drying Time Before Next Layer |
| Charged-Modified Surface Layer | Optional layer between ECM and hydrogel | Enhances selective cell adhesion (negative charge for IWECs, neutral/slight positive for OWECs) | 2-10 μm | 1-4 hours |
| Hydrogel Coating (Thin Film Application) | Trabecular meshwork-facing surface only | Supports endothelial migration, prevents shear stress damage | 10-500 μm | 6-24 hours |
| Hydrogel Cladding (Encapsulation Form) | Encapsulating stent or selected surfaces | Stages, endothelial release, dissolves over 3-14 days | 500-3000 μm | 24-48 hours |

Stepwise Cell Seeding Process

Stepwise seeding begins with the application of IWECs to the inner portion of the external surface of the endothelial stent 118, ensuring their placement facing the trabecular meshwork 108 rather than inside the stent lumen. IWECs may be pipetted onto the designated surface or infused via a syringe with a cannula to ensure targeted delivery. After allowing initial attachment, non-adherent cells are gently rinsed away to prevent random distribution.

Once IWECs are established, OWECs are seeded onto the outer surface of the endothelial stent 118, preferably near the collector channels 302, where they function as a non-fenestrated barrier to direct aqueous fluid 204 into the outflow pathways. OWECs are applied using the same pipetting or infusion method, followed by a gentle rinse to remove any unbound cells.

Charge Modification and Hydrogel Encapsulation for Selective Cell Attachment

The endothelial stent 118 may incorporate charge-modified surfaces to enhance selective endothelial cell 1402 attachment. The inner portion of the external surface can be negatively charged to attract IWECs, while the outer surface can be neutral or slightly positively charged to promote adhesion of OWECs.

Alternatively, a hydrogel coating 1108, 1208 encapsulation system can be applied to embed IWECs onto the inner portion of the external surface, while ensuring OWEC attachment on the outer surface. This method enhances cell retention and functionality before implantation.

Incubation and Pre-Conditioning Before Implantation

After seeding, the endothelial stent 118 may be incubated for approximately five days, allowing sufficient time for cell attachment and early differentiation before implantation. During this period, the endothelial cells 1402 can be pre-conditioned in a bioreactor system, where exposure to simulated aqueous fluid 204 flow facilitates maturation and functional adaptation.

By ensuring precise endothelial cell 1402 placement, biocompatible material selection, and optimal pre-implantation conditioning, this approach enhances the effectiveness of Schlemm's canal 104 endothelial stent 118 in restoring physiological aqueous fluid 204 outflow and regulating intraocular pressure in glaucoma treatment.

Stent-Seeding with Endothelial Progenitor Cells (EPC)

Traditional cell-based strategies rely on direct transplantation of fully differentiated endothelial cells 1402. However, mature endothelial cells 1402 derived from Schlemm's canal 104 may be limited by availability, expansion potential, and viability after implantation. In some embodiments of an endothelial-seeded stent 118, stem cell-derived endothelial cells 1402 instead of mature endothelial cells 1402 from Schlemm's canal 104 may be used. However, endothelial progenitor cells (EPCs) are preferred due to their enhanced safety profile and differentiation efficiency in Schlemm's canal 104 environments.

EPCs provide a self-renewing, plastic, and scalable alternative, allowing for post-implantation differentiation into Schlemm's canal-like endothelial cells 1402 that support aqueous fluid 204 outflow regulation. EPCs have been extensively studied for their ability to differentiate into functional endothelial cells 1402 in vascular and ocular environments. When exposed to physiological fluid shear stress, ECM proteins, and growth factors such as vascular endothelial growth factor (VEGF) and nitric oxide (NO)-releasing compounds, EPCs can acquire morphological and functional properties characteristic of Schlemm's canal 104 endothelium, including pore formation and mechanosensitive regulation of aqueous fluid 204 outflow resistance.

These progenitor cells can be harvested from multiple sources, including bone marrow, circulating blood, mesenchymal stem cells (MSCs), and induced pluripotent stem cells (iPSCs), providing a more accessible and patient-specific cell source than cadaveric Schlemm's canal 104 endothelial cells 1402. The ability to expand and precondition EPCs in a fluid-flow bioreactor before implantation further enhances their functional integration and long-term viability within Schlemm's canal 104.

The use of EPCs offers several key advantages over traditional Schlemm's canal 104 endothelial cell 1402 transplantation. The key differences in cell preparation for Schlemm's canal 104 endothelial cell 1402 (SCEE) and endothelial progenitor cells (EPC) are summarized in Table 16.

TABLE 16

Summary of EPC-Specific Modifications

| Seeding Step | Same as SCECs | Modified for EPCs |
|---|---|---|
| Cell Preparation | EGM-2 with VEGF, bFGF | Additional NO-releasing compounds to enhance differentiation |
| ECM Coating | Fibronectin, Laminin, Collagen IV | Add Heparan Sulfate, Hyaluronic Acid for enhanced adhesion |
| Cell Seeding | 100,000-200,000 cells per stent | Pre-expose to mild shear stress before seeding |
| Bioreactor Flow Conditioning | 1-6 dynes/cm$^2$ | Gradually increase shear stress over 3-5 days |
| Media Composition | Growth factors to maintain function | Gradual removal of VEGF/bFGF post-adhesion to simulate Schlemm's canal |

Summary of Stent Embodiments

The present inventions provide three general forms of an implantable endothelial stent 118 with the following embodiments:

1. Microporous or Nanotextured Outer Surface—Engineered to enhance endothelial cell 1402 attachment and migration along Schlemm's canal 104.
2. Bioactive Coatings—May include anti-inflammatory agents, adhesion peptides, or extracellular matrix proteins to support cell integration.
3. Flexible, Conformable Structure—Designed to minimize mechanical trauma and maintain canal curvature for optimal function.
4. Smart Degradable Membranes (Optional)—The endothelial stent 118 may include a biodegradable polymeric coating that gradually releases endothelial cells 1402 and then dissolves, leaving an endothelialized surface behind.
5. Bioactive Coatings—Can include anti-inflammatory agents, adhesion peptides, or extracellular matrix proteins to support cell integration.
6. Flexible, Conformable Structure—Designed to minimize mechanical trauma and maintain canal curvature for optimal function.

Those skilled in the art will appreciate that the exemplary embodiments and descriptions thereof are merely illustrative of the inventions as a whole. Any dimensions used herein are for example, and any dimension may be modified without changing the scope of the claims. While the principles of the inventions have been made clear in the exemplary embodiments, it will be obvious to those skilled in the art that modifications of the structure that modifications of the structure, arrangement, proportions, elements, and materials may be utilized in the practice of the inventions, which are particularly adapted to specific environments and operative requirements without departing from the principles of the inventions.

The invention claimed is:

1. An apparatus comprising:

a bioengineered stent configured for insertion in Schlemm's canal;

a biocompatible polymer scaffold, coated with collagen, affixed to the bioengineered stent;

endothelial cells adhered to the biocompatible polymer scaffold; and a cell-seeding system promoting endothelial cell adhesion and functional integration on an exterior surface of the bioengineered stent.

2. The apparatus of claim 1, wherein the biocompatible polymer scaffold includes fenestrated flow channels aligned with an anatomical curvature of Schlemm's canal.

3. The apparatus of claim 1, wherein the biocompatible polymer scaffold comprises surface ridges or microchannels.

4. The apparatus of claim 1, further comprising micropores on the bioengineered stent.

5. The apparatus of claim 4, wherein the micropores range from 0.5-2 microns, and the micropores are uniformly distributed.

6. The apparatus of claim 4, wherein the micropores range from 0.5-2 microns, and the micropores are asymmetrically positioned.

7. The apparatus of claim 1, wherein the biocompatible polymer scaffold further comprises a titanium oxide coating.

8. The apparatus of claim 1, wherein the biocompatible polymer scaffold comprises poly(L-lactic acid) (PLLA).

9. The apparatus of claim 8, wherein the poly(L-lactic acid) (PLLA) is configured to degrade over a period of three to six months.

10. The apparatus of claim 1, wherein the biocompatible polymer scaffold comprises cross-linked polyethylene glycol (PEG) hydrogel.

11. The apparatus of claim 10, wherein the cross-linked polyethylene glycol (PEG) hydrogel has a degradation time of two weeks to three months.

12. The apparatus of claim 1 wherein the bioengineered stent is seeded with the endothelial cells selected from a group consisting of mature Schlemm's canal endothelial cells, endothelial progenitor cells (EPCs), or stem cell-derived endothelial-like cells.

13. The apparatus of claim 1, wherein the biocompatible polymer scaffold is configured for visualization using optical coherence tomography (OCT), such that the biocompatible polymer scaffold permits in vivo imaging of endothelial coverage post-implantation.

14. The apparatus of claim 13, wherein the biocompatible polymer scaffold is optimized for swept-source OCT.

15. The apparatus of claim 1, wherein the biocompatible polymer scaffold is also coated with laminin or fibronectin.

16. The apparatus of claim 1, wherein the biocompatible polymer scaffold further comprises a surface coating of extracellular matrix proteins.

17. The apparatus of claim 1, wherein the biocompatible polymer scaffold further comprises a drug-eluting matrix releasing mitomycin C.

18. The apparatus of claim 1, wherein the bioengineered stent is configured for minimized trauma during delivery via microcatheter insertion.

19. The apparatus of claim 1, wherein the endothelial cells are derived from human Schlemm's canal tissue.

20. The apparatus of claim 1, wherein a polymer in the biocompatible polymer scaffold is a hybrid composite of silicone and polycaprolactone (PCL).

21. The apparatus of claim 1, wherein the biocompatible polymer scaffold is sterilized using gamma irradiation prior to cell seeding.

22. The apparatus of claim 1, wherein the biocompatible polymer scaffold includes a therapeutic coating comprising anti-inflammatory agents.

23. The apparatus of claim 1, wherein the biocompatible polymer scaffold includes a retention ring.

24. A bioengineered endothelial-seeded stent for Schlemm's canal, comprising:

a biocompatible polymer scaffold coated with collagen;

a stent-seeding system promoting endothelial adhesion and functional integration; and micropores configured for pressure-responsive aqueous humor drainage.

25. The bioengineered endothelial-seeded stent of claim 24 wherein the biocompatible polymer scaffold comprises:

a nitinol frame with a self-expanding structure; and a biodegradable polymer selected from a group consisting of poly(lactic-co-glycolic acid) (PLGA), polyethylene glycol (PEG), or polydimethylsiloxane (PDMS), each with a controlled degradation profile.

26. The bioengineered endothelial-seeded stent of claim 24, wherein the biocompatible polymer scaffold includes both a permanent and a bioabsorbable layer.

27. The bioengineered endothelial-seeded stent of claim 24, wherein the biocompatible polymer scaffold further comprises a titanium oxide coating.

28. The bioengineered endothelial-seeded stent of claim 24, further comprising a microporous structure in walls of the bioengineered endothelial-seeded stent, wherein the micropores range from 0.5-2 μm, and the micropores are uniformly distributed.

29. The bioengineered endothelial-seeded stent of claim 24, further comprising a microporous structure in walls of the bioengineered endothelial-seeded stent, wherein the micropores range from 0.5-2 μm, and the micropores are asymmetrically positioned.

30. An endothelial-seeded stent for implantation in Schlemm's canal, comprising:

a biocompatible polymer scaffold coated with collagen configured to support endothelial cell adhesion and function, a plurality of micropores configured to facilitate controlled aqueous humor outflow, wherein the endothelial-seeded stent is seeded with endothelial cells selected from a group consisting of:

Schlemm's canal endothelial cells (SCECs), endothelial progenitor cells (EPCs) capable of differentiating into Schlemm's canal-like endothelial cells, or a combination thereof, wherein the endothelial cells are conditioned to enhance integration and function within Schlemm's canal.

* * * * *